US011414362B2

(12) United States Patent
Iaccino et al.

(10) Patent No.: US 11,414,362 B2
(45) Date of Patent: Aug. 16, 2022

(54) PROCESSES AND SYSTEMS FOR THE CONVERSION OF HYDROCARBONS

(71) Applicant: ExxonMobil Chemical Patents Inc., Baytown, TX (US)

(72) Inventors: Larry L. Iaccino, Seabrook, TX (US); John S. Coleman, Houston, TX (US); James R. Lattner, La Porte, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 70 days.

(21) Appl. No.: 16/979,374

(22) PCT Filed: Mar. 1, 2019

(86) PCT No.: PCT/US2019/020323
§ 371 (c)(1),
(2) Date: Sep. 9, 2020

(87) PCT Pub. No.: WO2019/182744
PCT Pub. Date: Sep. 26, 2019

(65) Prior Publication Data
US 2021/0002186 A1 Jan. 7, 2021

Related U.S. Application Data

(60) Provisional application No. 62/647,010, filed on Mar. 23, 2018.

(51) Int. Cl.
*C07C 5/32* (2006.01)
*B01J 8/08* (2006.01)
(Continued)

(52) U.S. Cl.
CPC ............. *C07C 5/321* (2013.01); *B01J 8/082* (2013.01); *B01J 8/087* (2013.01);
(Continued)

(58) Field of Classification Search
CPC .. C07C 5/321; C07C 2/42; C07C 2/46; C07C 13/15; C07C 2601/10; C07C 5/32;
(Continued)

(56) References Cited

U.S. PATENT DOCUMENTS 5,525,311 A * 6/1996 Girod .................... B01J 8/0403
422/198
5,538,700 A * 7/1996 Koves ................... F28D 9/0031
422/198

(Continued)

OTHER PUBLICATIONS

Stears, B. (2016) "Implementation Challenges and Risk Mitigation for New Technology," Dow Olefins, Aromatics and Alternatives, *AICHE 2016 Natural Gas Utilization Conf.*, Morgantown, WV, 18 pgs.

(Continued)

*Primary Examiner* — Ali Z Fadhel

(57) ABSTRACT

A process for endothermic dehydrogenation including contacting a catalyst material in a moving bed reactor having at least one reaction zone, the moving bed reactor comprising a heat exchanger containing a heating medium, wherein the catalyst material and the heating medium do not contact one another, and wherein at least 50% of the delta enthalpy of the at least one reaction zone is provided by the heat exchanger; and contacting a feedstock comprising hydrocarbons with the catalyst material in the at least one reaction zone of the moving bed reactor under reaction conditions to convert at least a portion of the hydrocarbons to a first effluent comprising a product comprising alkenes, alkynes, cyclic hydrocarbons, and/or aromatics.

25 Claims, 8 Drawing Sheets

(51) Int. Cl.
*C07C 13/15* (2006.01)
*C07C 2/42* (2006.01)
*C07C 2/46* (2006.01)

(52) U.S. Cl.
CPC ............ *B01J 2208/00132* (2013.01); *B01J 2208/00141* (2013.01); *B01J 2208/00539* (2013.01); *B01J 2208/00557* (2013.01); *C07C 2/42* (2013.01); *C07C 2/46* (2013.01); *C07C 13/15* (2013.01)

(58) Field of Classification Search
CPC .. B01J 8/082; B01J 8/087; B01J 2208/00132; B01J 2208/00141; B01J 2208/00539; B01J 2208/00557
See application file for complete search history.

(56) References Cited

U.S. PATENT DOCUMENTS

| | | | | |
|---|---|---|---|---|
| 5,540,899 A * | 7/1996 | Koves | ............... | B01J 8/0207 165/113 |
| 5,600,052 A * | 2/1997 | Girod | ............... | F28D 9/0006 585/654 |
| 6,143,943 A * | 11/2000 | Oroskar | ............... | B01J 19/249 585/921 |
| 9,725,382 B2 | 8/2017 | Pretz et al. | ............... | C07C 5/3337 |
| 9,815,040 B2 | 11/2017 | Pretz et al. | ............... | B01J 8/18 |
| 9,834,496 B2 | 12/2017 | Pretz et al. | ............... | C07C 5/3337 |
| 9,873,647 B2 | 1/2018 | Iaccino | ............... | C07C 5/373 |
| 9,908,825 B1 | 3/2018 | Iaccino et al. | ............... | C07C 5/373 |
| 9,926,242 B2 | 3/2018 | Iaccino et al. | ............... | C07C 5/373 |
| 10,155,702 B2 | 12/2018 | Iaccino et al. | ............... | C07C 5/373 |
| 10,155,703 B2 | 12/2018 | Iaccino et al. | ............... | C07C 5/373 |
| 10,280,127 B1 | 5/2019 | Iaccino et al. | ............... | C07C 5/373 |
| 10,364,200 B2 | 7/2019 | Sangar et al. | ............... | C07C 5/3337 |
| 2002/0052534 A1* | 5/2002 | Lenglet | ............... | C07C 5/32 585/314 |
| 2004/0199039 A1* | 10/2004 | Brophy | ............... | B01F 33/30 585/660 |
| 2005/0119515 A1 | 6/2005 | Machhammer et al. | ............... | C07C 5/327 |
| 2006/0020047 A1* | 1/2006 | Wilkerson | ............... | C07C 409/08 528/86 |
| 2006/0115387 A1* | 6/2006 | Louret | ............... | B01J 8/0492 422/142 |
| 2006/0122446 A1* | 6/2006 | Louret | ............... | B01J 8/087 422/139 |
| 2008/0025885 A1* | 1/2008 | Zhou | ............... | B01J 29/90 422/600 |
| 2008/0027254 A1* | 1/2008 | Zhou | ............... | C07C 2/76 585/415 |
| 2009/0318742 A1* | 12/2009 | Xie | ............... | C10G 3/49 585/640 |
| 2018/0050315 A1* | 2/2018 | Gattupalli | ............... | F28D 7/00 |
| 2018/0051912 A1* | 2/2018 | Gattupalli | ............... | B01J 8/062 |
| 2018/0319717 A1 | 11/2018 | Sangar et al. | ............... | C07C 2/52 |
| 2019/0023998 A1* | 1/2019 | Sundaram | ............... | C10G 57/00 |

OTHER PUBLICATIONS

Zhaohui, M. et al. (2016) "Experimental Study of Integrated Ebullated-bed and Fixed-bed for Hydrotreating Mid-Low Temperature Coal Tar and Clean Fuel," *China Pet. Proc. and Petrochem. Tech.*, v.18(3), pp. 1-6.

* cited by examiner

PROCESSES AND SYSTEMS FOR THE CONVERSION OF HYDROCARBONS

CROSS-REFERENCE OF RELATED APPLICATIONS

This application is a 371 National Phase entry of International Application No. PCT/US2019/020323 filed 1 Mar. 2019, which claims the benefit of Provisional Application No. 62/647,010, filed Mar. 23, 2018, the disclosures of which are incorporated herein by reference.

FIELD OF THE INVENTION

This invention relates to processes and reactor systems for the conversion of hydrocarbons to alkenes, alkynes, cyclic hydrocarbons, and/or aromatics.

BACKGROUND OF THE INVENTION

Olefins (an alkene) are a class of unsaturated hydrocarbon compounds containing at least one pair of carbon atoms, the carbon atoms of the pair being directly linked by a double bond. Since the double-bonded carbons allow the compounds to be reacted with a wide variety of other compounds to produce a wide array of useful products, olefin compounds are of considerable commercial importance.

Olefins are produced commercially by a variety of processes, for example, steam cracking and fluid catalytic cracking of saturated hydrocarbons. Since these processes produce olefin having a range of molecular weights, and typically also other non-olefin products, technologies such as catalytic dehydrogenation processes have been developed to yield specific olefins having a particular number of carbon atoms. Catalytic dehydrogenation includes catalytically reacting (i.e., dehydrogenating) a saturated hydrocarbon compound such as alkane to produce a desired olefin, alkyne, cyclic hydrocarbon, and/or aromatic.

A particularly desirable olefin product is propylene and cyclopentadiene. Catalytic dehydrogenation technologies include those that catalytically react propane to produce propylene; or the reaction of pentane to produce, for example, cyclopentadiene ("CPD"), and/or its dimer dicyclopentadiene ("DCPD"). Catalytic dehydrogenation also includes catalytically reacting olefins to produce a desired dialkene, alkyne, cyclic hydrocarbon, and/or aromatic. Catalytic dehydrogenation may also include alkylation reactions in conjunction with dehydrogenation, such as catalytically reacting methane to form benzene. These reactions are highly endothermic so must be conducted at high temperature and heat supplied to the reaction to achieve commercially attractive conversion levels.

There are a number of commercial dehydrogenation processes including the CATOFIN® process (Lummus), the OLEFLEX™ process (Honeywell UOP), the steam active reforming (STAR PROCESS™) (Uhde), the fluidized bed dehydrogenation (FBD) process (Snamprogetti-Yarsintez), and the Linde-BASF fixed bed process.

The CATOFIN™ process, which is based on the Houdry Catadiene process for isobutane dehydrogenation to isobutene, dehydrogenates propane in 5-8 parallel adiabatic fixed-bed reactors containing a chromia-alumina catalyst. Process conditions include a temperature of approximately 575-650° C. and a pressure between 0.2 and 0.5 bar. Heat is supplied by frequently stopping propane feed to the reactors and heating the catalyst beds to high temperature with combustion product gas.

Another fixed-bed process, the STAR PROCESS™, operates at a pressure of 6 to 9 bar and a temperature of between 500° C. to 600° C. Steam is added to the alkane feed to reduce alkane partial pressure, resulting in less coke formation. The feed is conducted to a first reactor, which contains a catalyst comprising Pt—Sn supported on a (basic) zinc-aluminate. A calcium/magnesium-aluminate binder is used to stabilize the catalyst in the presence of the steam. The catalyst is located in tubes and heat is supplied by external firing; significant radial thermal gradients exist within the tubes. The gas mixture exiting the first reactor is cooled prior to being introduced into the second reactor (called an oxyreactor), where an oxygen-steam mixture is used to selectively combust part of the hydrogen formed during the dehydrogenation. Combusting the hydrogen shifts equilibrium toward higher olefin yields but a portion of the hydrocarbon feed is also combusted producing CO and $CO_2$.

Like the STAR PROCESS™, the Linde-BASF dehydrogenation process is a fixed bed reactor process, using an alkane feed diluted with steam. The catalyst comprises Pt—Sn supported on $ZrO_2$. The catalyst is located in tubes and heat is supplied by external firing; significant radial thermal gradients exist within the tubes.

The OLEFLEX™ process uses a settling bed with Pt—Sn-based catalyst in a multiple radial flow, settling bed reactors in series operating at pressures between 1 and 3 bar and a temperature of 525° C. to 705° C. Heat is supplied by preheating the feed and reheating the partially converted stream in between each of the reactors.

A fluidized-bed process, FBD, incorporates the use of a fluid catalytic cracking reactor system. The alkane feed flows through a staged fluidized bed reactor, contacting the alkane with heated $CrO_x/Al_2O_3$ catalyst promoted with an alkali metal. The alkane dehydrogenation is carried out at a pressure of 1.1 to 1.5 bar and a temperature of 550° C. to 600° C. Carbon deposits formed on the catalyst during the dehydrogenation, resulting in deactivated catalyst. The deactivated catalyst is transported to a regenerator connected to the reactor to combust the carbon deposits, which reactivates the catalyst for reuse. Fuel gas is added to the regenerator to provide sufficient heat so that a hot catalyst can be returned to the reactor to supply the heat of reaction. The regenerated catalyst is returned to the fluidized bed reactor at a temperature significantly higher than the target heat outlet temperature.

In each of the foregoing examples, heat is introduced to the reactor in such a way that at least a portion of the catalyst and/or at least a portion of the hydrocarbon stream are exposed to undesirably high temperatures resulting in catalyst deactivation/damage and/or undesirable reactions such as cracking to lower carbon number hydrocarbons and production of coke (i.e., nonvolatile hydrocarbon).

Since the catalytic dehydrogenation of olefins is an equilibrium reaction, process conditions affect the amount of olefin that can be produced. An example of such a reaction is the dehydrogenation of propane to produce propylene: $C_3H_8 \leftrightarrows C_3H_6 + H_2$ ($\Delta H^0_{298}$=124.3 kJ $mol^{-1}$). Thus, heat (124.3 kJ $mol^{-1}$) is required to dehydrogenate propane, which means that the reaction is an endothermic reaction. Typically, dehydrogenation of $C_2$-$C_4$ alkane to produce $C_2$-$C_4$ olefin requires a reaction temperature in the range of 550° C. to 750° C., with the conversion of the alkane being about 50% at about 1 bar.

Higher conversions of alkane to olefin can be obtained by increasing the reaction temperature and/or reducing the hydrogen gas (molecular hydrogen) partial pressure. However, raising the temperature can reduce selectivity to desired olefin and result in additional undesirable byproducts being produced through one or more undesired hydrogenolysis, cracking, and isomerization side reactions (e.g., increased feed cracking to methane).

What is desired is an alternative process for an alkane dehydrogenation reaction. Processes for converting alkane to a desired product at high conversion of the alkane and high selectivity to the desired product are particularly desired.

SUMMARY OF THE INVENTION

Disclosed is a process for endothermic dehydrogenation comprising contacting a catalyst material in a moving bed reactor having at least one reaction zone, the moving bed reactor comprising a heat exchanger containing a heating medium, wherein the catalyst material and the heating medium do not contact one another, and wherein at least 50% of the delta enthalpy of the at least one reaction zone is provided by the heat exchanger; and contacting a feedstock comprising hydrocarbons with the catalyst material in the at least one reaction zone of the moving bed reactor under reaction conditions to convert at least a portion of the hydrocarbons to a first effluent comprising a product comprising alkenes, alkynes, cyclic hydrocarbons, and/or aromatics.

Nonlimiting examples of the hydrocarbons in the feedstock comprise acyclic $C_2$-$C_{10}$ hydrocarbons that include, but are not limited to, alkanes (e.g., ethane, propane, butane, pentane, hexane, etc.), alkenes (e.g., ethylene, propylene, butylene, etc.), alkynes (e.g., ethyne, propyne, 1-butyne, 2-butyne, etc.), dialkenes (e.g., 1,2-propadiene, 1,3-butadiene, 1,3-pentadiene, etc.), and any combination thereof.

Nonlimiting examples of the catalyst material comprise at least one metal or metal compound comprising at least one selected from the group consisting of V, Nb, Ta, Cr, Mo, W, Mn, Re, Fe, Ru, Os, Co, Rh, Ir, Ni, Pd, Pt, Cu, Ag, Au, Zn, Cd, Al, Ga, In, Tl, Ge, Sn, Pb, and any combination thereof.

Nonlimiting examples of the particulate movement in the at least one reaction zone of the moving bed reactor are a bubbling regime, a turbulent regime, and/or a transport regime.

Nonlimiting examples of the heating medium comprise steam, a combustion product, a hot gas, a molten salt, and/or a molten metal.

The heat exchanger can traverse at least a portion of the at least one reaction zone. Alternatively, the heat exchanger does not traverse at least a portion of the at least one reaction zone. In any instance, the heat exchanger comprises a heat transfer conduit. Nonlimiting examples of heat transfer conduit configurations include a plurality of bayonet tubes in a vertical, bottom-feed configuration; a plurality of bayonet tubes in a vertical, top-feed configuration; a plurality of tubes in a horizontal configuration; a plurality of tubes in a vertical configuration; and any combination thereof.

Optionally, a baffle is present in the at least one reaction zone, and the at least one reaction zone includes two reaction zones and on opposing sides of the baffle.

Optionally, the process can further comprise: separating at least some of the catalyst material from the first effluent to produce (1) a separated catalyst stream (which can optionally be substantially catalyst-free) and (2) a product stream; and returning the separated catalyst material to the moving bed reactor. The product stream can, for example, exit the moving bed reactor at an outlet temperature of about 350° C. to about 800° C., wherein a cumulative exposure time of a hydrocarbon fluid phase to temperatures 50° C. greater than the outlet temperature is less than 10% of total exposure time, and wherein a cumulative exposure time of the catalyst material to temperatures 50° C. greater than the outlet temperature is less than 10% of total catalyst material time in the moving bed reactor.

The process can optionally further include contacting the heat exchanger with an auxiliary gas stream comprising steam, inert gas, hydrogen, and/or light hydrocarbons, wherein the auxiliary gas stream and the heating medium do not contact.

The process can optionally further include transferring at least a portion of the catalyst material to a rejuvenation zone and/or a regeneration zone to produce a rejuvenated catalyst material and/or a regenerated catalyst material; and returning at least a portion of the rejuvenated catalyst material and/or the regenerated catalyst material to the at least one reaction zone.

The process can optionally further include contacting the feedstock with a transport particulate material that has selective hydrogen combustion, hydrogen storage, and/or oxidant storage functionality.

DETAILED DESCRIPTION OF THE INVENTION

I. Definitions

Figure 1A:
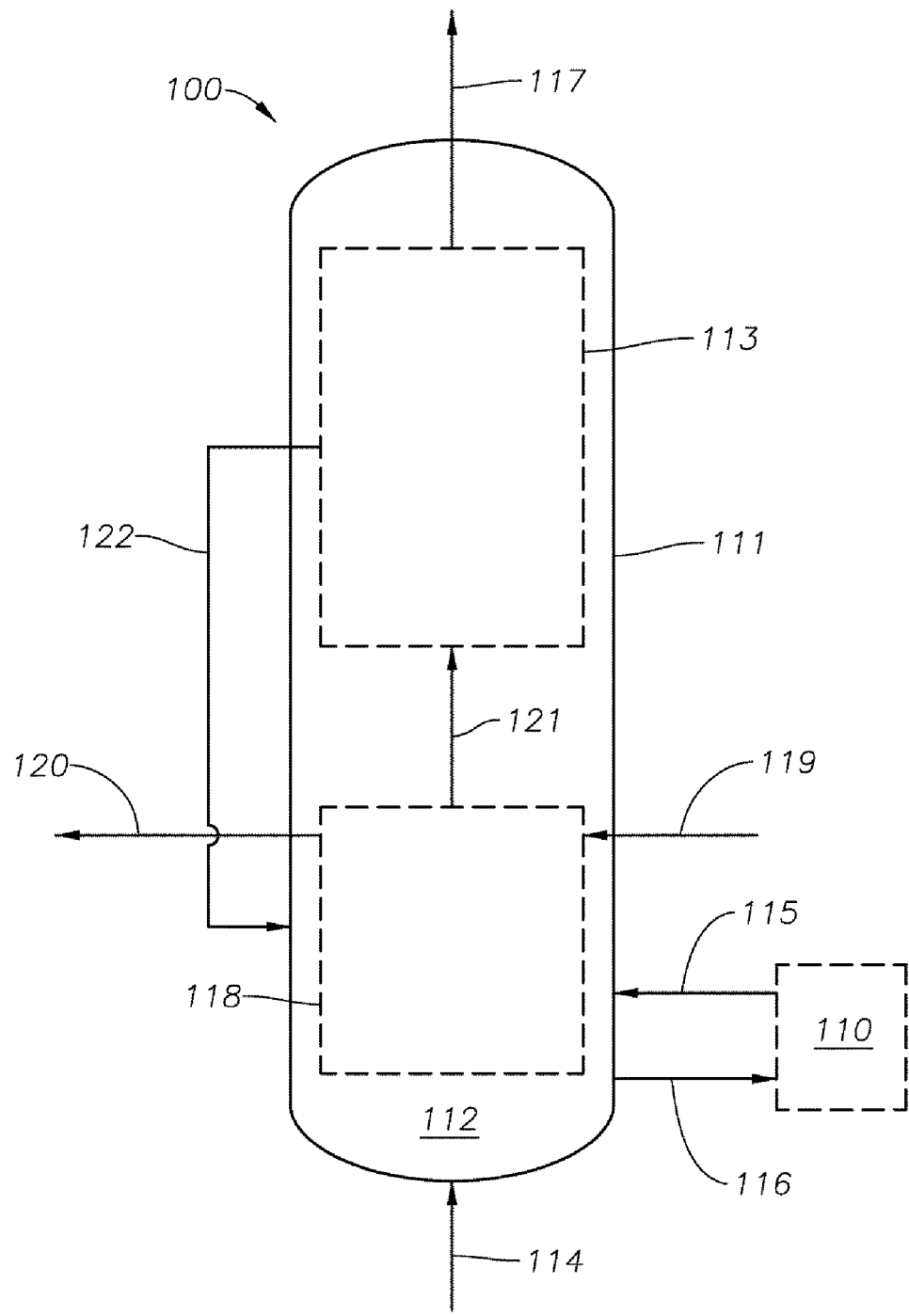
FIG. 1A shows an example of an endothermic dehydrogenation reactor system.

To facilitate an understanding of the present invention, a number of terms and phrases are defined below.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n. The term "$C_n$" means hydrocarbon(s) having n carbon atom(s) per molecule, wherein n is a positive integer.

As used herein, the term "light hydrocarbon" means light paraffinic and/or olefinic hydrocarbons comprised substantially of hydrogen and carbon only and has one to no more than 4 carbon atoms.

The term "saturated hydrocarbon" refers to hydrocarbons having no multiple bonding and includes, but is not limited to, alkanes and cycloalkanes.

The term "unsaturated hydrocarbon" refers to hydrocarbons having at least one carbon-carbon double bond and includes, but is not limited to, alkenes, dialkenes, alkynes, cyclo-alkenes, and cyclo-dialkenes.

The term "cyclic hydrocarbon" denotes groups such as the cyclopropane, cyclopropylene, cyclobutane, cyclobutadiene etc., and substituted analogues of these structures. These cyclic hydrocarbons can be single- or multi-ring structures. Preferably, the term "cyclic hydrocarbon" refers to non-aromatics.

The term "cyclic $C_5$" includes, but is not limited to, cyclopentane, cyclopentene, cyclopentadiene, and mixtures of two or more thereof. The term "cyclic $C_5$" also includes alkylated analogs of any of the foregoing, e.g., methyl cyclopentane, methyl cyclopentene, and methyl cyclopentadiene. It should be recognized for purposes of the invention that cyclopentadiene spontaneously dimerizes over time to form dicyclopentadiene via Diels-Alder condensation over a range of conditions, including ambient temperature and pressure.

The term "acyclic hydrocarbon" includes, but is not limited to, linear and branched saturated and non-saturated hydrocarbons.

The term "alkane" refers to non-aromatic saturated hydrocarbons with the general formula $C_nH_{(2n+2)}$, where n is 1 or greater. An alkane may be straight chained or branched. Examples of alkanes include, but are not limited to, methane, ethane, propane, butane, pentane, hexane, heptane and octane. "Alkane" is intended to embrace all structural isomeric forms of an alkane. For example, butane encompasses n-butane and isobutane; pentane encompasses n-pentane, isopentane and neopentane.

The term "alkene," alternatively referred to as "olefin," refers to a branched or unbranched unsaturated hydrocarbon having one or more carbon-carbon double bonds. A simple alkene comprises the general formula $C_nH_{2n}$, where n is 2 or greater. Examples of alkenes include, but are not limited to, ethylene, propylene, butylene, pentene, hexene and heptene. "Alkene" is intended to embrace all structural isomeric forms of an alkene. For example, butylene encompasses but-1-ene, (Z)-but-2-ene, etc.

The term "aromatic" means a planar cyclic hydrocarbyl with conjugated double bonds, such as benzene. As used herein, the term aromatic encompasses compounds containing one or more aromatic rings, including, but not limited to, benzene, toluene, and xylene, and polynuclear aromatics (PNAs), which include naphthalene, anthracene, chrysene, and their alkylated versions. The term "$C_{6+}$ aromatics" includes compounds based upon an aromatic ring having six or more ring atoms, including, but not limited to, benzene, toluene, and xylene, and polynuclear aromatics (PNAs), which include naphthalene, anthracene, chrysene, and their alkylated versions.

The term "coke" includes, but is not limited to, a low hydrogen content hydrocarbon that is adsorbed on the catalyst composition.

The term "$C_5$ feedstock" includes a feedstock containing n-pentane, such as a feedstock which is predominately normal pentane and isopentane (also referred to as methylbutane), with smaller fractions of cyclopentane and neopentane (also referred to as 2,2-dimethylpropane).

The term "dehydrogenation" includes chemical reactions that involve removal of hydrogen from an organic molecule. Dehydrogenation in the present disclosure may be oxidative or non-oxidative. Further, dehydrogenation in the present disclosure encompasses dehydrogenation in conjunction with coupling such as conversion of methane, $C_2$, $C_3$, $C_4$, and $C_5$ hydrocarbons to aromatics.

All numbers and references to the Periodic Table of Elements are based on the new notation as set out in 63(5) CHEMICAL AND ENGINEERING NEWS 27 (1985), unless otherwise specified.

The term "Group 10 metal" means an element in Group 10 of the Periodic Table and includes, but is not limited to, Ni, Pd, and Pt, and a mixture of two or more thereof.

The term "Group 11 metal" means an element in Group 11 of the Periodic Table and includes, but is not limited to, Cu, Ag, Au, and a mixture of two or more thereof.

The term "Group 1 alkali metal" means an element in Group 1 of the Periodic Table and includes, but is not limited to, Li, Na, K, Rb, Cs, and a mixture of two or more thereof, and excludes hydrogen.

The term "Group 2 alkaline earth metal" means an element in Group 2 of the Periodic Table and includes, but is not limited to, Be, Mg, Ca, Sr, Ba, and a mixture of two or more thereof.

The term "rare earth metal" means an element in the Lanthanide series of the Periodic Table, as well as scandium and yttrium. The term rare earth metal includes, but is not limited to, lanthanum, praseodymium, neodymium, cerium, yttrium, and a mixture of two or more thereof.

The term "oxygen" includes air, $O_2$, $H_2O$, CO, and $CO_2$.

As used herein, the term "molecular sieve of the MCM-22 family" (or "material of the MCM-22 family" or "MCM-22 family material" or "MCM-22 family zeolite") includes one or more of: molecular sieves made from a common first degree crystalline building block unit cell, which unit cell has the MWW framework topology. (A unit cell is a spatial arrangement of atoms, which if tiled in three-dimensional space describes the crystal structure. Such crystal structures are discussed in the "Atlas of Zeolite Framework Types", Fifth edition, 2001); molecular sieves made from a common second degree building block, being a 2-dimensional tiling of such MWW framework topology unit cells, forming a monolayer of one unit cell thickness, preferably one c-unit cell thickness; molecular sieves made from common second degree building blocks, being layers of one or more than one unit cell thickness, wherein the layer of more than one unit cell thickness is made from stacking, packing, or binding of at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "microporous crystalline material" or "zeolite."

As used herein, the term "selectivity" means the moles of carbon in the respective cyclic $C_5$, CPD, $C_1$, and $C_{2-4}$ formed divided by total moles of carbon in the pentane converted. For example, the term "carbon selectivity to cyclic $C_5$ of at least 30%" means that at least 30 moles of carbon in the cyclic $C_5$ is formed per 100 moles of carbon in the pentane converted.

As used herein, the term "conversion" means the moles of carbon in the acyclic $C_5$ feedstock that is converted to a product. The phrase "a conversion of at least 70% of said acyclic $C_5$ feedstock to said product" means that at least 70% of the moles of said acyclic $C_5$ feedstock was converted to a product.

As used herein, the "Alpha Value" of a molecular sieve catalyst is a measure of the cracking activity of that catalyst using n-hexane conversion at 538° C. in a Quartz plug flow reactor at atmospheric pressure. Catalytic cracking activity is typically indicated by the weight percent conversion of hexane to lower boiling C1 to C5 hydrocarbons. The experimental conditions of the test include sizing the catalyst to 14-25 mesh and diluting with quartz, and heating the catalyst to a constant temperature of 538° C. and exposure to the feed in the plug flow reactor. The feed consists of a mixture of n-hexane in helium, at a hexane partial pressure of 100 Torr (133 mbar). The WHSV is adjusted to keep the hexane conversion between 5 and 25%. Four data points are measured at 4 minutes, 11 minutes, 18 minutes, and 25 minutes time on stream. The reported Alpha value is taken after 18 min time of stream. The n-hexane cracking activity, expressed as Alpha, is defined as the first order rate constant for n-hexane conversion relative to a silica-alumina standard (amorphous aluminosilicate catalyst obtained by co-gellation, 10% alumina, surface area of 420 m$^2$/g, no cations in base exchanging solution), and determined using formula: $\alpha = A \cdot \ln(1-X)/\tau$; where "$\alpha$" is the relative first order rate constant, and:

"A" includes the reference rate constant and unit conversion=−1.043;
"X" is the fractional conversion;
"τ" is the residence time=wt/(ρ·F);
"ρ" is the packing density in g/cm$^3$;
"F" is the gas flow rate in cm$^3$/min;
"wt" is the catalyst weight in g.

Alpha Values for some typical catalysts are: ZSM-5 with no cation exchange (38), and with H$^+$ exchange (450); synthetic Faujasite exchanged in calcium ions (1.1), and exchanged in H(NH$_4$) (6,400).

In any embodiment, the catalyst composition described herein has an Alpha Value (as measured prior to the addition of the Group 10 metal, preferably platinum) of less than 25, alternately less than 15, alternately from 1 to 25, alternately from 1.1 to 15.

As used herein, the term "dehydrogenation reactor system" refers to a system including one or more reactors and all necessary and optional equipment used in dehydrogenation reactions.

As used herein, the term "reactor" refers to any vessel(s) in which a chemical reaction occurs. Reactor includes both distinct reactors, as well as reaction zones within a single reactor apparatus and, as applicable, reactions zones across multiple reactors. In other words, and as is common, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

A reactor/reaction zone may be an adiabatic reactor/reaction zone or a diabatic reactor/reaction zone. As used herein, the term "adiabatic" refers to a reaction zone for which there is essentially no heat input into the system other than by a flowing process fluid. A reaction zone that has unavoidable losses due to conduction and/or radiation may also be considered adiabatic for the purpose of this invention. As used herein, the term "diabatic" refers to a reactor/reaction zone to which heat is supplied by a means in addition to that provided by the flowing process fluid.

As used herein, the term "moving bed" reactor refers to a zone or vessel with contacting of solids (e.g., catalyst particles) and gas flows such that the superficial gas velocity (U) is sufficient to fluidize solid particles (i.e., above the minimum fluidization velocity $U_{mf}$)A moving bed reactor may operate under several flow regimes including, bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$), where $U_{mf}$ is minimum fluidizing velocity, $U_{mb}$ is minimum bubbling velocity, $U_c$ is the velocity at which fluctuation in pressure peaks, and $U_{tr}$ is transport velocity. These different fluidization regimes have been described in, for example, Kunii, D., Levenspiel, O., Chapter 3 of FLUIDIZATION ENGINEERING, (2$^{nd}$ Edition, Butterworth-Heinemann, Boston, 1991), and Walas, S. M., Chapter 6 of CHEMICAL PROCESS EQUIPMENT, (Revised 2nd Edition, Butterworth-Heinemann, Boston, 2010).

A moving bed reactor may be a "circulating moving bed reactor," which refers to a moving bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor. Additionally, a moving bed reactor may be a "captive bed reactor" wherein solids (e.g., catalyst material) may circulate between reaction zones but are not circulated, on a continuous flow basis, between the reactor and a separate vessel (e.g., to perform re-heating and/or regeneration). Solids (e.g., catalyst material) may be withdrawn from the reactor and returned (along with any fresh solids addition) to the reactor after batchwise regeneration performed in a separate vessel. Also, presence of an external cyclone (or any similar device to separate solids from the reactor effluent stream) and its return standpipe is considered part of the captive moving bed reactor (i.e., does not constitute a separate vessel) for the purpose of defining a captive moving bed reactor. As used herein, the term "transport" reactor (also known as a riser reactor) refers to a zone or vessel (such as, vertical cylindrical pipe) used for net upwards transport of solids (e.g., catalyst particles) in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in Kunii, D., Levenspiel, O., Chapter 3 of FLUIDIZATION ENGINEERING, (2nd Edition, Butterworth-Heinemann, Boston, 1991) and Walas, S. M., Chapter 6 of CHEMICAL PROCESS EQUIPMENT, (Revised 2nd Edition, Butterworth-Heinemann, Boston, 2010). A fluidized bed reactor, such as a circulating fluidized bed reactor, may be operated as a transport reactor. "Average diameter" for particles in the range of 1 to 3500 µm is determined using a to MASTERSIZER™ 3000 available from Malvern Instruments, Ltd., Worcestershire, England. Unless otherwise stated, particle size is determined at D50. D50 is the value of the particle diameter at 50% in the cumulative distribution. For example, if D50=5.8 µm, then 50% of the particles in the sample are equal to or larger than 5.8 µm and 50% are smaller than 5.8 µm. In contrast, if D90=5.8 µm, then 10% of the particles in the sample are larger than 5.8 µm and 90% are smaller than 5.8 µm.

"Average diameter" for particles in the range of 3 mm to 50 mm is determined using a micrometer on a representative sample of 100 particles.

For purposes of the invention, 1 psi is equivalent to 6.895 kPa. Likewise, 1 psig is equivalent to 6.895 kPa gauge (kPa-g).

II. Hydrocarbon Conversion Process

This invention relates to a dehydrogenation process for converting hydrocarbons to alkenes, cyclic hydrocarbons, and/or aromatics in a reactor system. The process may comprise heating the catalyst material, optionally in at least one reaction zone and/or in at least one heating, non-reaction zone, with a heat exchanger having a heating medium contained therein such that the catalyst and heating medium do not contact. When heating the catalyst material occurs in at least one reaction zone, the at least one reaction zone is also heated by the heat exchanger. When heating the catalyst material occurs in at least one heating, non-reaction zone, the heated catalyst and corresponding carrier gas, at least in part, heat the at least one reaction zone. Further, the process may comprise contacting a feedstock comprising hydrocarbons and optionally hydrogen and/or optionally steam or light hydrocarbon with a catalyst material in at least one reaction zone under reaction conditions to convert at least a portion of the hydrocarbons to a first effluent comprising alkenes, cyclic hydrocarbons, and/or aromatics. The at least one reaction zone and/or the at least one heating, non-reaction zone has a temperature of about 500° C. to about 1100° C. The heating medium has a temperature of about 600° C. to about 1300° C. entering the heat exchanger and a temperature of about 500° C. to about 850° C. leaving the heat exchanger. Optionally, the process may further comprise providing an auxiliary gas comprising hydrogen, alkanes (e.g., $C_1$-$C_4$ alkanes) and/or alkenes (e.g., $C_1$-$C_4$ alkenes) at a temperature of about 300° C. to about 1000° C. to optionally further heat the at least one reaction zone. In any embodiment, the feedstock enters the at least one reaction zone at a temperature of about 300° C. to about 800° C. Additionally, the feedstock and the auxiliary gas may be provided to the at least one reaction zone at different locations via different inlets.

The dehydrogenation process can, for example, be for conversion of an acyclic $C_5$ feedstock to a product comprising cyclic $C_5$ compounds (e.g., cyclopentadiene). The process comprising the steps of contacting said feedstock and, optionally, hydrogen under acyclic $C_5$ conversion conditions in the presence of one or more catalyst compositions, including, but not limited to, the catalyst compositions described herein, and providing an auxiliary gas as described herein to form said product.

The product of the process for conversion of an acyclic $C_5$ feedstock comprises cyclic $C_5$ compounds comprising one or more of cyclopentane, cyclopentene, cyclopentadiene, and any combination thereof. The cyclic $C_5$ compounds can comprise at least about 20 wt %, or 30 wt %, or 40 wt %, or 70 wt % cyclopentadiene, or in the range of from about 10 wt % to about 80 wt %, alternately 20 wt % to 70 wt %.

The acyclic $C_5$ conversion conditions can include at least a temperature, an n-pentane partial pressure, and a weight hourly space velocity (WHSV). The temperature is in the range of about 400° C. (or 450° C. or 500° C.) to about 700° C. (or 650° C. or 600° C.). The n-pentane partial pressure is in the range of about 3 psia to about 100 psia (or 50 psia or 20 psia) at the reactor inlet. The WHSV is in the range from about 1 $hr^{-1}$ to about 50 $hr^{-1}$ (or 20 $hr^{-1}$). Such conditions include a molar ratio of the optional hydrogen to the acyclic $C_5$ feedstock in the range of about 0 (or 1) to 3 (or 2). Such conditions may also include $C_1$-$C_4$ hydrocarbons with the acyclic $C_5$ feed.

The process for conversion of n-pentane to cyclopentadiene can, for example, comprise the steps of contacting n-pentane and, optionally, hydrogen (if present, typically $H_2$ is present at a ratio to n-pentane of 0.01 to 3.0) with one or more catalyst compositions, including but not limited to, the catalyst compositions described herein, and providing an auxiliary gas as described herein to form cyclopentadiene at a temperature of 400° C. to 700° C., an n-pentane partial pressure of 3 to about 100 psia at the reactor inlet, and a weight hourly space velocity of 1 to about 50 $hr^{-1}$.

Alternatively, the dehydrogenation process can, for example, be for converting ethane to ethylene, propane to propylene, and/or butane to butenes. Conversion conditions for such a process can include temperatures in the range from about 400° C. (or 450° C. or 500° C.) to about 700° C. (or 650° C. or 600° C. or 550° C.). The feedstock for this example dehydrogenation process can include greater than or equal to about 50 mole % (or 75 mole % or 95 mole %) alkane (i.e., ethane, propane, and/or butane). The WHSV can be in the range from about 0.1 $hr^{-1}$ to about 100 $hr^{-1}$ (or 50 $hr^{-1}$ or 20 $hr^{-1}$). Such conditions include a molar ratio of the optional hydrogen to the alkane feedstock in the range of about 0 (or 1) to 3 (or 2).

Alternatively, the dehydrogenation process can, for example, be for converting methane to aromatics. Conversion conditions for such a process can include temperatures in the range from about 500° C. (or 550° C. or 600° C.) to about 1000° C. (or 950° C. or 900° C. or 800° C.) and pressures in the range of about 10 psia (or 15 psia or 20 psia) to about 100 psia (or 75 psia or 60 psia). Optional ethane, hydrogen, water, carbon monoxide, and/or carbon dioxide can be included in the feedstock with methane. The feedstock for this example dehydrogenation process can include greater than or equal to about 90 mole % (or 95 mole % or 99 mole %) methane and, when included, less than or equal to about 10 mole % (or 5 mole % or 1 mole %) of one or more other gases. The WHSV can be in the range from about 0.1 $hr^{-1}$ to about 100 $hr^-$ (or 50 $hr^{-1}$ or 20 $hr^{-1}$).

A. Feedstock and Optional Auxiliary Gas

In the process, a feedstock comprising hydrocarbons, preferably acyclic $C_2$-$C_{10}$ hydrocarbons, are provided to a reactor system comprising a catalyst material and an inert material. Acyclic $C_2$-$C_{10}$ hydrocarbons include, but are not limited to, alkanes (e.g., ethane, propane, butane, pentane, hexane, etc.), alkenes (e.g., ethylene, propylene, butylene, etc.), alkynes (e.g., ethyne, propyne, 1-butyne, 2-butyne, etc.), dialkenes (e.g., 1,2-propadiene, 1,3-butadiene, 1,3-pentadiene, etc.), and any combination thereof. An acyclic $C_2$-$C_{10}$ hydrocarbon feedstock, useful herein, is obtainable from crude oil or natural gas condensate. Optionally, hydrogen may be present in the feedstock as well. The molar ratio of optional hydrogen to hydrocarbon is between about 0 (or 1) to about 3 (or 2). Hydrogen may be included in the feedstock in order to minimize production of coke material on the particulate material and/or to fluidize the particulate material in the at least one reaction zone.

The feedstock comprises at least about 50 wt %, or 60 wt %, or 75 wt %, or 90 wt % hydrocarbons (e.g., in the range from about 50 wt % (or 60 wt % or 75 wt % or 90 wt %) to about 100 wt % (or 95 wt % or 90 wt %)). The amount of the hydrocarbons in the feedstock converted to acyclic alkenes (e.g., acyclic pentenes and acyclic pentadienes), cyclic hydrocarbons (e.g., cyclopentane, cyclopentene, and cyclopentadiene) and/or aromatics (e.g., benzene) is greater than or equal to about 5 wt %, 10 wt %, 20 wt %, 30 wt %, 40 wt %, 50 wt %, 60 wt %, 70 wt %, 80 wt %, or 90 wt % (e.g., in the range from about 5 wt % (or 25 wt % or 50 wt %) to about 100 wt % (or 95 wt % or 90 wt % or 75 wt %)).

For example when converting an acyclic $C_5$ feedstock to a product comprising cyclic $C_5$ compounds, the feedstock may preferably comprise an acyclic $C_5$ feedstock and can include cracked $C_5$ (in various degrees of unsaturation: alkenes, dialkenes, alkynes) produced by refining and chemical processes, such as fluid catalytic cracking (FCC), reforming, hydrocracking, hydrotreating, coking, and steam cracking. For example, the acyclic $C_5$ feedstock useful in the process comprises pentane, pentene, pentadiene and mixtures of two or more thereof. The acyclic $C_5$ feedstock comprises, for example, at least about 50 wt %, or 60 wt %, or 75 wt %, or 90 wt % n-pentane, or in the range from about 50 wt % to about 100 wt % n-pentane.

The acyclic $C_5$ hydrocarbon feedstock optionally does not comprise $C_6$ aromatic compounds, such as benzene. When present, $C_6$ aromatic compounds are present at less than 5 wt %, or 1 wt %, or 0.01 wt %. Additionally, or alternatively, the hydrocarbon feedstock optionally does not comprise benzene, toluene, or xylene (ortho, meta, or para). When present, any benzene, toluene, or xylene (ortho, meta, or para) compounds are present at less than 5 wt %, or 1 wt %, or 0.01 wt %.

The acyclic $C_5$ hydrocarbon feedstock optionally does not comprise $C_{6+}$ paromatic compounds. When present, $C_{6+}$ aromatic compounds are present at less than 5 wt %, or 1 wt %, or 0.01 wt %.

When converting an acyclic $C_5$ feedstock to a product comprising cyclic $C_5$ compounds, an amount of the $C_5$ hydrocarbons (e.g., acyclic $C_5$ hydrocarbons) in the feedstock converted to cyclopentadiene is greater than or equal to about 5 wt %, 10 wt %, 20 wt %, 30 wt %, 40 wt %, 50 wt %, 60 wt %, 70 wt %, 80 wt %, or 90 wt % (e.g., about 5% (or 10 wt %, or 20 wt %) to about 90 wt % (or 80 wt %, or 70 wt %, or 60 wt %)).

Optionally, auxiliary gas comprising steam, inert gas, hydrogen, and/or light hydrocarbons (e.g., $C_1$-$C_5$ hydrocarbons, preferably $C_1$-$C_4$ hydrocarbons such as $C_1$-$C_4$ alkenes and/or $C_1$-$C_4$ alkanes) is also fed into the at least one reaction zone (discussed herein).

The auxiliary gas can comprise greater than or equal to about 25 wt %, or 50 wt %, or 60 wt %, or 75 wt %, or 90 wt % hydrogen (e.g., in the range from about 25 wt % (or 50 wt %, or 60 wt %, or 70 wt %) to about 100 wt % (or 90 wt % or 80 wt %) hydrogen). The auxiliary gas can comprise greater than or equal to about 25 wt %, or 50 wt %, or 60 wt %, or 75 wt %, or 90 wt % light hydrocarbons (e.g., in the range from about 25 wt % (or 50 wt %, or 60 wt %, or 70 wt %) to about 100 wt % (or 90 wt % or 80 wt %) light hydrocarbons). The auxiliary gas can comprise greater than or equal to about 25 wt %, or 50 wt %, or 60 wt %, or 75 wt %, or 90 wt % inert gas (e.g., in the range from about 25 wt % (or 50 wt %, or 60 wt %, or 70 wt %) to about 100 % (or 90 wt % or 80 wt %) inert gas). The auxiliary gas can comprise greater than or equal to about 25 wt %, or 50 wt %, or 60 wt %, or 75 wt %, or 90 wt % steam (e.g., in the range from about 25 wt % (or 50 wt %, or 60 wt %, or 70 wt %) to about 100 wt % (or 90 wt % or 80 wt %) steam). For example, the auxiliary gas may comprise hydrogen, ethane, methane, and/or a mixture of ethane and ethylene.

Preferably, the feedstock and auxiliary gas are substantially free of oxygen (e.g., less than about 1.0 wt %, or 0.1 wt %, or 0.01 wt %, or 0.001 wt %, or 0.0001 wt %, or 0.00001 wt %).

The feedstock and the auxiliary gas may be provided to the at least one reaction zone at different locations via different inlets. The feedstock and the auxiliary gas may be provided to the at least one reaction zone simultaneously or not, preferably simultaneously. It is contemplated herein that auxiliary gas and the feedstock are provided to the at least one reaction zone in different horizontal and/or vertical planes. For example, the auxiliary gas may be provided to the at least one reaction zone at a lower position in the at least one reaction zone with respect to where the feedstock is provided (e.g., the feedstock may be provided to the at least one reaction zone at a position above (or higher than) where the auxiliary gas is provided). For example, the auxiliary gas and the feedstock may be provided to the at least one reaction zone at different horizontal planes, preferably where the auxiliary gas is provided at a horizontal plane at a lower position in the at least one reaction zone with respect to horizontal plane where the feedstock is provided, and optionally, the auxiliary gas and the feedstock may be provided along the same or different vertical plane. Alternatively, the auxiliary gas and the feedstock may be provided to the at least one reaction zone at different horizontal planes, preferably where the auxiliary gas is provided at a horizontal plane above (or higher than) a horizontal plane where the feedstock is provided, and optionally, the auxiliary gas and the feedstock may be provided along the same or different vertical plane. Additionally, it is contemplated herein that the feedstock and the auxiliary gas may be provided to the at least one reaction zone at substantially the same locations via the same or different inlet.

Hydrogen may be provided to the reactor via the feedstock, the auxiliary gas, or a combination of both. Preferably, hydrogen is included in both the feedstock and the auxiliary gas. The presence of hydrogen in the feed mixture at or near the inlet location, where the feed first comes into contact with the catalyst, can prevent or reduce the formation of coke on the catalyst particles. Additionally, the presence of hydrogen in the auxiliary gas can prevent or reduce the formation of coke in auxiliary gas pre-heating furnaces.

B. Reaction Zone

The feedstock is fed into a dehydrogenation reactor system and contacted with a catalyst material in at least one reaction zone under reaction conditions to convert at least a portion of the hydrocarbons (e.g., acyclic $C_5$ hydrocarbons) to a first effluent comprising alkenes (e.g., propylene), cyclic hydrocarbons (e.g., cyclopentadiene), and/or aromatics (e.g., benzene). The at least one reaction zone can be one reaction zone that is the moving bed reactor. For example, the moving bed reactor may be a circulating moving bed reactor or a captive moving bed reactor. The moving bed reactor may be operated in a bubbling, turbulent, fast fluidization, or transport regime, as described in Kunii, D., Levenspiel, O., Chapter 3 of FLUIDIZATION ENGINEERING, ($2^{nd}$ Edition, Butterworth-Heinemann, Boston, 1991), and Walas, S. M., Chapter 6 of CHEMICAL PROCESS EQUIPMENT, (Revised $2^{nd}$ Edition, Butterworth-Heinemann, Boston, 2010). Additionally, or alternatively, the at least one reaction zone is not a radial-flow reactor or a cross-flow reactor.

Additionally, or alternatively, the at least one reaction zone may comprise at least a first reaction zone, a second reaction zone, a third reaction zone, a fourth reaction zone, a fifth reaction zone, a sixth reaction zone, a seventh reaction zone, and/or an eighth reaction zone, etc. As understood herein, each reaction zone may be an individual reactor or a reactor may comprise one or more of the reaction zones. The dehydrogenation reactor system includes 1 (or 2, or 4) to 20 (or 15, or 10, or 8) reaction zones. Where the at least one reaction zone includes a first and a second reaction zone, the reaction zones may be arranged in any suitable configuration (e.g., in series). Each reaction zone independently may be a moving bed. Additionally, or alternatively, the process described herein may further comprise moving a bulk of a partially converted feedstock from the first reaction zone to the second reaction zone and/or moving a bulk of a particulate material (e.g., catalyst material and/or inert material) from the second reaction zone to the first reaction zone. As used herein, "bulk" refers to at least a majority portion of the partially converted feedstock and the particulate material (e.g., portions of at least about 50 wt %, or 60 wt %, or 70 wt %, or 80 wt %, or 90 wt %, or 95 wt %, or 99.0 wt %, or 100 wt %).

The at least one reaction zone may include at least one internal structure (e.g., 1, 2, 3, 4, 5, 6, 7, 8, 9, 10, 15, 20, 30, 40, 50, etc.) to influence a velocity vector of the particulate material and/or gas flow. Further, the internal structure(s) can ensure movement of particulate material while minimizing the degree of gas back-mixing. Particularly, the at least one reaction zone may include a plurality of internal structures. Nonlimiting examples of suitable internal structures include a plurality of baffles, sheds, trays, tubes, tube bundles, tube coils, rods, and/or distributors.

The at least one reaction zone is operated under reaction conditions sufficient to convert at least a portion of the hydrocarbons feedstock to a first effluent comprising alkenes, alkynes, cyclic hydrocarbons, and/or aromatics. The feedstock (e.g., hydrocarbons) and/or auxiliary may be fed to the reaction system at a weight hourly space velocity (WHSV, mass of hydrocarbons/mass of catalyst/hour) in the range of from about 0.1 hr$^{-1}$ (or 1.0 hr$^{-1}$, or 2.0 hr$^{-1}$, or 5 hr$^{-1}$) to about 1000 hr$^{-1}$ (or 900 hr$^{-1}$, or 800 hr$^{-1}$, or 700 hr$^{-1}$, or 600 hr$^{-1}$, or 500 hr$^{-1}$, or 400 hr$^{-1}$, or 300 hr$^{-1}$, or 200 hr$^{-1}$, or 100 hr$^{-1}$, or 90 hr$^{-1}$, or 80 hr$^{-1}$, or 70 hr$^{-1}$, or 60 hr$^{-1}$, or 50 hr$^{-1}$, or 40 hr$^{-1}$, or 30 hr$^{-1}$, or 20 hr$^{-1}$).

Production of alkenes, alkynes, cyclic hydrocarbons, and/or aromatics from hydrocarbons is accomplished via endothermic reactions, which present various challenges, such as maintaining high temperatures required for the reactions including transferring a large amount of heat to a catalyst. Advantageously, the heat exchanger may provide the endothermic heat of reaction for the conversion process within the at least one reaction zone. In any embodiment, the heat exchanger can provide greater than or equal to about 50%, or 55%, or 60%, or 65%, or 70%, or 75%, or 80%, or 85%, or 90%, or 95%, or equal to about 100% (e.g., in a range of about 50% (or 55%, or 60%, or 65%, or 70%, or 75%) to about 100% (or 95%, or 90%, or 85%, or 80%, or 75%, or 70%)) of the delta enthalpy to the at least one reaction zone. As used herein, the term "delta enthalpy of the at least one reaction zone" refers to the enthalpy of effluent of the at least one reaction zone at conditions at which the effluent leaves the at least one reaction zone minus the enthalpy of feedstock and auxiliary gas at conditions at which they are introduced to the at least one reaction zone.

When an auxiliary gas is included, the auxiliary gas may optionally be preheated. In particular, the auxiliary gas provided to the at least one reaction may provide less than about 50%, or 45%, or 40%, or 35%, or 30%, or 25%, or 20%, or 15%, or 10%, or 5%, or equal to 0% (e.g., in a range of about 0% (or 5%, or 10%, or 15%, or 20%, or 25%, or 30%) to less than about 50% (or 45%, or 40%, or 35%, or 30%, or 25%)) of the delta enthalpy to the at least one reaction zone. The auxiliary gas may enter the at least one reaction zone at a temperature of greater than or equal to about 350° C., or 400° C., or 450° C., or 500° C., or 550° C., or 600° C., or 650° C., or 700° C., or 750° C., or 800° C., or 850° C., or 900° C., or 950° C., or 1000° C., or 1050° C., or 1100° C., or 1150° C., or 1200° C., or 1250° C., or 1300° C. (e.g., in a range of about 350° C. (or 400° C., or 450° C., or 500° C., or 550° C., or 600° C., or 650° C., or 700° C., or 750° C., or 800° C.) to about 1300° C. (or 1250° C., or 1200° C., or 1150° C., or 1100° C., or 1050° C., or 1000° C., or 950° C., or 900° C., or 850° C.)).

The feedstock may optionally be preheated. In particular, the feedstock provided to the at least one reaction may provide less than about 50%, or 45%, or 40%, or 35%, or 30%, or 25%, or 20%, or 15%, or 10%, or 5%, or equal to 0% (e.g., in a range of about 0% (or 5%, or 10%, or 15%, or 20%, or 25%, or 30%) to less than about 50% (or 45%, or 40%, or 35%, or 30%, or 25%)) of the delta enthalpy to the at least one reaction zone. The feedstock may enter the at least one reaction zone at a temperature of greater than or equal to about 300° C., or 350° C., or 400° C., or 450° C., or 500° C., or 550° C., or 600° C., or 650° C., or 700° C., or 750° C., or 800° C., or 850° C., or 900° C., or 950° C., or 1000° C. (e.g., in a range of about 300° C. (or 350° C., or 400° C., or 450° C., or 500° C., or 550° C., or 600° C., or 650° C., or 700° C., or 750° C., or 800° C.) to about 1000° C. (or 950° C., or 900° C., or 850° C., or 800° C., or 750° C., or 700° C., or 650° C.)). For example, when the feedstock comprises $C_3$-$C_6$, the feedstock may enter the at least one reaction zone at a temperature of greater than or equal to about 300° C., or 350° C., or 400° C., or 450° C., or 500° C., or 550° C., or 600° C., or 650° C., or 700° C., or 750° C. (e.g., in a range of about 300° C. (or 350° C., or 400° C., or 450° C., or 500° C., or 550° C.) to about 750° C. (or 700° C., or 650° C., or 600° C.)). In another example, when the feedstock comprises methane and/or ethane, the feedstock may enter the at least one reaction zone at a temperature of greater than or equal to about 500° C., or 550° C., or 600° C., or 650° C., or 700° C., or 750° C., or 800° C., or 850° C., or 900° C., or 950° C., or 1000° C. (e.g., in a range of about 500° C. (or 550° C., or 600° C., or 650° C., or 700° C., or 750° C., or 800° C.) to about 1000° C. (or 950° C., or 900° C., or 850° C., or 800° C., or 750° C., or 700° C., or 650° C.)).

Additionally, it may be preferable that an isothermal or substantially isothermal temperature profile be maintained in the at least one reaction zone. A substantially isothermal temperature profile has the advantages of maximizing the effective utilization of the catalyst and minimizing the production of undesirable $C_4$-byproducts. As used herein, "isothermal temperature profile" means that the temperature at each point within the reaction zone between the reactor inlet and reactor outlet as measured along the tube centerline of the reactor is kept essentially constant, e.g., at the same temperature or within the same narrow temperature range wherein the difference between an upper temperature and a lower temperature is no more than about 40° C.; more preferably no more than about 20° C. Preferably, the isothermal temperature profile is one where the temperature along the length of the reaction zone(s) within the reactor does not vary by more than about 40° C. as compared to the average temperature within the reactor, alternately not more than about 20° C., alternately not more than about 10° C., alternately not more than about 5° C. Alternately, the isothermal temperature profile is one where the temperature along the length of the reaction zone(s) within the reactor is within about 20% of the average temperature within the reactor, alternately within about 10%, alternately within about 5%, alternately within about 1% of the average temperature within the reactor.

The temperature of a first effluent exiting the at least one reaction zone at an effluent outlet may be greater than or equal to about 400° C., or 450° C., or 500° C., or 550° C., or 600° C., or 650° C., or 700° C., or 750° C., or 800° C., or 850° C., or 900° C., (e.g., in a range of about 400° C. (or 425° C., or 450° C., or 475° C., or 500° C., or 525° C., or 550° C., or 575° C., or 600° C., or 650° C., or 700° C.) to about 900° C. (or 875° C., or 850° C., or 800° C., or 750° C., or 700° C., or 675° C., or 650° C., or 625° C., or 600° C., or 575° C.)). For example, when the feedstock comprises $C_3$-$C_6$, the temperature of a first effluent exiting the at least one reaction zone at an effluent outlet may be greater than or equal to about 400° C., or 450° C., or 500° C., or 550° C., or 600° C., or 650° C., or 700° C. (e.g., in a range of about 400° C. (or 425° C., or 450° C., or 475° C., or 500° C., or 525° C., or 550° C.) to about 700° C. (or 675° C., or 650° C., or 625° C., or 600° C., or 575° C.)). In another example, when the feedstock comprises methane and/or ethane, the temperature of a first effluent exiting the at least one reaction zone at an effluent outlet may be greater than or equal to about 600° C., or 650° C., or 700° C., or 750° C., or 800° C., or 850° C., or 900° C., (e.g., in a range of about 600° C. (or 625° C., or 650° C., or 700° C.) to about 900° C. (or 875° C., or 850° C., or 800° C., or 750° C., or 725° C.)).

The temperature in the at least one reaction zone at an effluent outlet may be greater than or equal to about 300° C., or 350° C., or 400° C., or 450° C., or 500° C., or 550° C., or 600° C., or 650° C., or 700° C., or 750° C., or 800° C., or 850° C., or 900° C., (e.g., in a range of about 300° C. (or 350° C., or 400° C., or 425° C., or 450° C., or 475° C., or 500° C., or 525° C., or 550° C., or 575° C., or 600° C., or 650° C., or 700° C.) to about 900° C. (or 875° C., or 850° C., or 800° C., or 750° C., or 700° C., or 675° C., or 650° C., or 625° C., or 600° C., or 575° C.)). For example, when the feedstock comprises $C_3$-$C_6$, the temperature in the at least one reaction zone at an effluent outlet may be greater than or equal to about 300° C., or 350° C., or 400° C., or 450° C., or 500° C., or 550° C., or 600° C., or 650° C., or 700° C. (e.g., in a range of about 300° C. (or 350° C., or 400° C., or 425° C., or 450° C., or 475° C., or 500° C., or 525° C., or 550° C.) to about 700° C. (or 675° C., or 650° C., or 625° C., or 600° C., or 575° C.)). In another example, when the feedstock comprises methane and/or ethane, the temperature in the at least one reaction zone at an effluent outlet may be greater than or equal to about 500° C., or 550° C., or 600° C., or 650° C., or 700° C., or 750° C., or 800° C., or 850° C., or 900° C., (e.g., in a range of about 500° C. (or 550° C., or 600° C., or 625° C., or 650° C., or 700° C.) to about 900° C. (or 875° C., or 850° C., or 800° C., or 750° C., or 725° C.)).

The reaction conditions at the effluent outlet of the at least one reaction zone may include a pressure of greater than or equal to about 1.0 psia (or 2.0 psia, or 3.0 psia, or 4.0 psia, or 5 psia, or 10 psia, or 15 psia, or 20 psia, or 25 psia, or 30 psia, or 35 psia, or 40 psia, or 45 psia, or 50 psia, or 55 psia, or 60 psia, or 65 psia, or 70 psia, or 75 psia, or 80 psia, or 85 psia, or 90 psia, or 95 psia, or 100 psia, or 125 psia, or 150 psia, or 175 psia, or about 200 psia (e.g., in a range of about 1.0 psia (or 2.0 psia, or 3.0 psia, or 4.0 psia, or 5 psia) to about 200 psia (or 150 psia, or 100 psia, or 50 psia, or 25 psia)). For example, the reaction conditions at the effluent outlet of the at least one reaction zone may comprise a temperature of about 500° C. to about 700° C. and a pressure of about 3.0 psia to about 100 psia.

A delta pressure (or pressure drop) across the at least one reaction zone (pressure at feedstock inlet minus pressure at effluent outlet) may be greater than or equal to about 1.0 psia (or 2.0 psia, or 3.0 psia, or 4.0 psia, or 5 psia, or 10 psia, or 15 psia (e.g., in a range of about 1.0 psia (or 1.5 psia, or 2.0 psia) to about 15 psia (or 10 psia, or 8.0 psia, or 5 psia, or 3.0 psia))

As used herein, the term "hydrocarbon fluid phase" encompasses hydrocarbons in the feedstock, hydrocarbons in an auxiliary gas, reaction intermediates, and product hydrocarbons. In the present disclosure, the hydrocarbon fluid phase and catalyst minimally experience temperatures above the product outlet temperature. For example, a cumulative exposure time of the hydrocarbon fluid phase to temperatures about 50° C. greater than the product outlet temperature is less than about 10% of total exposure time (e.g., less than about 5% of total exposure time), and wherein a cumulative exposure time of the catalyst material to temperatures about 50° C. greater than the product outlet temperature is less than about 10% of total catalyst material time in the reactor (e.g., less than about 5% of total catalyst material time in the reactor). In another example, a cumulative exposure time of the hydrocarbon fluid phase to temperatures about 25° C. greater than the product outlet temperature is less than about 20% of total exposure time (e.g., less than about 10% of total exposure time), and wherein a cumulative exposure time of the catalyst material to temperatures about 25° C. greater than the product outlet temperature is less than about 20% of total catalyst material time in the reactor (e.g., less than about 10% of total catalyst material time in the reactor).

C. Catalyst Material, Inert Material, and Transport Particulate Material

The at least one reaction zone comprises particulate material including a catalyst material. The catalyst material, also referred to as a "catalyst composition" or "catalyst," is present in the reaction system for promoting conversion of at least a portion of the hydrocarbons to alkenes, alkynes, cyclic hydrocarbons, and/or aromatics.

Nonlimiting examples of catalyst materials comprise metals and/or metal compounds that comprise one or more of V, Nb, Ta, Cr, Mo, W, Mn, Re, Fe, Ru, Os, Co, Rh, Ir, Ni, Pd, Pt, Cu, Ag, Au, Zn, Cd, Al, Ga, In, Tl, Ge, Sn, Pb, and any combination thereof. Nonlimiting examples of metal compounds include metal oxides, metal sulfides, metal sulfates, metal phosphides, metal phosphates, metal carbides, metal nitrides, metal silicates, metal silicides, metal aluminates, and any combination thereof. The catalyst material can optionally further comprise a support (e.g., a high surface area, refractory support) for the metal and/or metal compound. Nonlimiting examples of supports include silica, alumina, titania, zirconia, chromia, zeolite, metallosilicate aluminum phosphate, and any combination thereof. Specific examples are included herein.

Dehydrogenation catalysts can include at least one metal selected from Groups 5-14 of the Periodic Table, including such metals in oxide and/or sulfide form. The catalyst thereof can further comprise at least one additional material utilized as binder, matrix, and/or support. Typically, such additional materials include one or more inorganic oxides or sulfides, especially those that are stable under process conditions specified for dehydrogenation, combustion, and re-oxidation. For example, the additional material can include one or more inorganic oxides of elements in Groups 13 and 14 of the Periodic Table, silica and/or alumina. The catalyst can include one or more mixed metal catalysts, meaning that the catalyst can comprise more than one metal element having non-oxidative alkane dehydrogenation functionality.

The dehydrogenation functionality of the catalyst can be provided by one or more of (i) Group 5 metals including V, Nb, and Ta, with V being preferred, (ii) Group 6 metals including Cr, Mo, W, with Cr and Mo being preferred, and Cr being particularly preferred, (iii) Group 7 metals including Mn and Re, with Mn being preferred, (iv) Group 8 metals including Fe, Ru and Os, with Fe being preferred, (v) Group 9 metals including Co, Rh and Ir, with Co being preferred, (vi) Group 10 metals including Ni, Pd and Pt, with Ni and Pt being preferred, and Pt being particularly preferred, (vii) Group 11 metals including Cu, Ag and Au, with Cu being preferred, (viii) Group 12 metals including Zn and Cd, with Zn being preferred, (ix) Group 13 metals including Al, Ga, In and Tl, with Ga and In being preferred, and (x) Group 14 metals including Ge, Sn and Pb, with Sn being preferred.

Specific examples of catalyst having non-oxidative alkane dehydrogenation catalytic activity under the specified dehydrogenation conditions include those listed in Two-Step Catalytic Oxidative Dehydrogenation of Propane: An Alternative Route to Propene, 97-9(4) ORGANIC PROCESS RESEARCH & DEVELOPMENT, 403 (2005). The catalytic metal is typically activated before use, e.g., by reducing the catalytic metal from a higher oxidation state to a lower one. Conventional methods can be utilized to do so, but the invention is not limited thereto.

Examples of platinum-based dehydrogenation catalysts include platinum supported on alumina and Pt/Sn supported on alumina. The platinum-based dehydrogenation catalysts can further comprise alkaline promoter. Additional metals such as Mg, Zn and/or Ca can be included in the catalyst. Conventional platinum-containing dehydrogenation catalysts can be used, but the invention is not limited thereto.

Catalysts having dehydrogenation activity derived from platinum, e.g., from platinum atoms, platinum ions, and/or platinum in platinum-containing compounds (collectively, platinum-based materials), are suitable for use in the process.

Chromium-based dehydrogenation catalysts are also suitable for use in the process. Examples of preferred chromium-containing active materials include chromia supported on alumina, such as those described in J. Gascon, et al., Propane Dehydrogenation over a $Cr_2O_3/Al_2O_3$ Catalyst: Transient Kinetic Modeling of Propane and Coke Formation, 248 APPLIED CATALYSIS A: GENERAL 105-116 (2003). The chromium-containing active materials can further comprise alkaline promoter.

Catalyst compositions useful herein also include microporous crystalline metallosilicates, such as crystalline aluminosilicates, crystalline ferrosilicates, or other metal-containing crystalline silicates (such as those where the metal or metal-containing compound is dispersed within the crystalline silicate structure and may or may not be a part of the crystalline framework). Microporous crystalline metallosilicate framework types useful as catalyst compositions herein include, but are not limited to, MWW, MFI, LTL, MOR, BEA, TON, MTW, MTT, FER, MRE, MFS, MEL, DDR, EUO, and FAU.

Particularly suitable microporous metallosilicates for use herein, include those of framework type MWW, MFI, LTL, MOR, BEA, TON, MTW, MTT, FER, MRE, MFS, MEL, DDR, EUO, and FAU (such as zeolite beta, mordenite, faujasite, Zeolite L, ZSM-5, ZSM-11, ZSM-22, ZSM-23, ZSM-35, ZSM-48, ZSM-50, ZSM-57, ZSM-58, and MCM-22 family materials) where one or more metals from groups 8, 11, and 13 of the Periodic Table of the Elements (preferably one or more of Fe, Cu, Ag, Au, B, Al, Ga, and/or In) are incorporated in the crystal structure during synthesis or impregnated post crystallization. It is recognized that a metallosilicate may have one of more metals present and, for example, a material may be referred to as a ferrosilicate, but it will most likely still contain small amounts of aluminum.

The microporous crystalline metallosilicates preferably have a constraint index of less than 12, alternately from 1 to 12, alternately from 3 to 12. Aluminosilicates useful herein have a constraint index of less than 12, such as 1 to 12, alternately 3 to 12, and include, but are not limited to, Zeolite beta, mordenite, faujasite, Zeolite L, ZSM-5, ZSM-11, ZSM-22, ZSM-23, ZSM-35, ZSM-48, ZSM-50, ZSM-57, ZSM-58, MCM-22 family materials, and mixtures of two or more thereof. For example, the crystalline aluminosilicate has a constraint index of about 3 to about 12 and is ZSM-5.

As used herein, the "Constraint Index" is a measure of the extent to which a microporous molecular sieve (e.g., zeolites, aluminosilicates) provides controlled access of different sized molecules to its internal structure. For example, molecular sieves which provide a highly restricted access to and egress from its internal structure have a high value for the Constraint Index, and molecular sieves of this kind usually have pores of small size, e.g. less than 5 Angstroms. On the other hand, molecular sieves which provide relatively free access to the internal molecular sieves structure have a low value for the Constraint Index, and usually pores of large size.

A determination of the Constraint Index is made by continuously passing a mixture of an equal weight of n-hexane and 3-methylpentane over a small molecular sieves catalyst sample, approximately 1 gram or less, of catalyst at atmospheric pressure. A sample of the catalyst, in the form of pellets or extrudate, is crushed to a particle size about that of coarse sand and mounted in a glass tube. Prior to testing, the catalyst is treated with a stream of air at 1000° F. (538° C.) for at least 15 minutes. The catalyst is then flushed with helium and the temperature adjusted between 550° F. (288° C.) and 950° F. (510° C.) to give an overall conversion between 10% and 60%. The mixture of hydrocarbons is passed at 1 liquid hourly spaced velocity (i.e., one volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons. The Constraint Index is then calculated using the following equation: Constraint Index=$Log_{10}$ (fraction of n-hexane remaining)/$Log_{10}$ (fraction of 3-methylpentane remaining). For details, see "The Constraint Index Revisited" in 35-36 MICROPOROUS AND MESOPOROUS MATERIALS 31-46 (2000). Constraint Index (CI) values for some typical catalysts are: Erinotite (38); ZSM-5 (8.3); ZSM-11 (8.7); ZSM-12 (2); ZSM-38 (2); ZSM-38 (4.5); synthetic Mordenite (0.5); REY (0.4); amorphous aluminosilicate (0.6).

ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573. ZSM-50 is described in U.S. Pat. No. 4,640,829. ZSM-57 is described in U.S. Pat. No. 4,873,067. ZSM-58 is described in U.S. Pat. No. 4,698,217.

The MCM-22 family material is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, and mixtures of two or more thereof.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), and ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve of the MCM-22 family For example, the crystalline metallosilicate has an Si/M molar ratio (where M is a group 8, 11, or 13 metal) greater than about 3, or greater than about 25, or greater than about 50, or greater than about 100, or greater than about 400, or in the range from about 100 to about 2,000, or from about 100 to about 1,500, or from about 50 to 2,000, or from about 50 to 1,200.

For example, the crystalline aluminosilicate has an $SiO_2/Al_2O_3$ molar ratio greater than about 3, or greater than about 25, or greater than about 50, or greater than about 100, or greater than about 400, or greater than about 1,000, or in the range from about 100 to about 400, or from about 100 to about 500, or from about 25 to about 2,000, or from about 50 to about 1,500, or from about 100 to about 1,200, or from about 50 to about 1,000.

Typically, the microporous crystalline metallosilicate (such as an aluminosilicate) is combined with a Group 10 metal or metal compound and, optionally, one, two, three, or more additional metals selected from Groups 8, 9, 11, and 13 of the Periodic Table of the Elements and the rare earth metals, such as Ga, In, Zn, Cu, Re, Mo, W, La, Fe, Ag, Rh, Pr, La, and/or oxides, sulfides, nitrides, and/or carbides of these metals. Alternatively, or additionally, the Group 10 metal is present in combination with a Group I alkali metal and/or a Group 2 alkaline earth metal.

For example, the Group 10 metal includes, or is selected from the group consisting of, Ni, Pd, and Pt, preferably Pt. The Group 10 metal content of said catalyst composition is at least 0.005 wt %, based on the weight of the catalyst composition. For example, the Group 10 content is in the range from about 0.005 wt % to about 10 wt %, or from about 0.005 wt % up to about 1.5 wt %, based on the weight of the catalyst composition.

The Group 1 alkali metal is generally present as an oxide and the metal is selected from the group consisting of lithium, sodium, potassium, rubidium, cesium, and mixtures of two or more thereof. The Group 2 alkaline earth metal is generally present as an oxide and the metal is selected from the group consisting of beryllium, magnesium, calcium, strontium, barium, and mixtures of two or more thereof.

For example, the Group 11 metal includes, or is selected from the group consisting of, silver, gold, copper, preferably silver or copper. The Group 11 metal content of said catalyst composition is at least 0.005 wt %, based on the weight of the catalyst composition. For example, the Group 11 content is in the range from about 0.005 wt % to about 10 wt %, or from about 0.005 wt % up to about 1.5 wt %, based on the weight of the catalyst composition. For example, the molar ratio of said Group 11 metal to Group 10 metal is at least about 0.1, or from at least about 0.1 up to about 10, preferably at least about 0.5, more preferably at least about 1. For example, the Group 11 metal is present as an oxide.

A preferred Group 9 metal is Rh, which may form an alloy with the Group 10 metal. Preferably, the molar ratio of Rh to Group 10 metal is in the range from about 0.1 to about 5.

Typically, the rare earth metal is selected from the group consisting of yttrium, lanthanum, cerium, praseodymium, and mixtures, and any combination thereof. Preferably, the molar ratio of rare earth metal to Group 10 metal is in the range from about 1 to about 10. The rare earth metal may be added to the catalyst composition during or after synthesis of the microporous crystalline molecular sieve as any suitable rare earth metal compound.

For example, in aluminosilicates, the molar ratio of said Group 1 alkali metal to Al is at least about 0.5, or from at least about 0.5 up to about 3, preferably at least about 1, more preferably at least about 2.

For example, in aluminosilicates, the molar ratio of said Group 2 alkaline earth metal to Al is at least about 0.5, or from at least about 0.5 up to about 3, preferably at least about 1, more preferably at least about 2.

For example, the use of any one of the catalyst compositions of this invention provides a conversion of at least about 70%, or at least about 75%, or at least about 80%, or in the range from about 60% to about 80%, of said acyclic $C_5$ feedstock under acyclic $C_5$ conversion conditions. This includes an n-pentane containing feedstock with equimolar $H_2$, a temperature in the range of about 550° C. to about 600° C., an n-pentane partial pressure between 3 and 10 psia, and an n-pentane weight hourly space velocity of 10 to 20 $hr^-$.

For example, the use of any one of the catalyst compositions of this invention provides a carbon selectivity to cyclic $C_5$ compounds of at least about 30%, or at least about 40%, or at least about 50%, or in the range from about 30% to about 80%, under acyclic $C_5$ conversion conditions. This includes an n-pentane feedstock with equimolar $H_2$, a temperature in the range of about 550° C. to about 600° C., an n-pentane partial pressure between 3 and 10 psia, and an n-pentane weight hourly space velocity between 10 and 20 $hr^{-1}$.

For example, the use of any one of the catalyst compositions of this invention provides a carbon selectivity to cyclopentadiene of at least about 30%, or at least about 40%, or at least about 50%, or in the range from about 30% to about 80%, under acyclic $C_5$ conversion conditions. This includes an n-pentane feedstock with equimolar $H_2$, a temperature in the range of about 550° C. to about 600° C., an n-pentane partial pressure between 3 and 10 psia, and an n-pentane weight hourly space velocity between 10 and 20 $hr^{-1}$.

The catalyst compositions of this invention can be combined with a matrix or binder material to render them attrition resistant and more resistant to the severity of the conditions to which they will be exposed during use in hydrocarbon conversion applications. The combined compositions can contain 1 to 99 wt % of the materials of the invention based on the combined weight of the matrix (binder) and material of the invention. The relative proportions of microcrystalline material and matrix may vary widely, with the crystal content ranging from about 1 to about 90 wt % and, more usually, particularly when the composite is prepared in the form of beads, extrudates, pills, oil drop formed particles, spray dried particles, etc., in the range of about 2 to about 80 wt % of the composite. Preferred binder materials comprise one or more of silica, titania, zirconia, metal silicates of Group 1 or Group 13 of the Periodic Table, carbides, nitrides, aluminum phosphate, aluminum molybdate, aluminate, surface passivated alumina, and mixtures thereof. Preferably, suitable binder materials have a lower affinity for Group 10 metal particles, e.g., Pt, in comparison with the crystalline metallosilicate, e.g., aluminosilicate.

Useful catalyst compositions comprise a crystalline aluminosilicate or ferrosilicate, which is optionally combined with one, two, or more additional metals or metal compounds.

Preferred combinations include: a crystalline aluminosilicate (such as ZSM-5 or Zeolite L) combined with a Group 10 metal (such as Pt), a Group 1 alkali metal (such as sodium or potassium) and/or a Group 2 alkaline earth metal; a crystalline aluminosilicate (such as ZSM-5 or Zeolite L) combined with a Group 10 metal (such as Pt), and a Group 1 alkali metal (such as sodium or potassium); a crystalline aluminosilicate (such as a ferrosilicate or an iron treated ZSM-5) combined with a Group 10 metal (such as Pt) and a Group 1 alkali metal (such as sodium or potassium); a crystalline aluminosilicate (Zeolite L) combined with a Group 10 metal (such as Pt) and a Group 1 alkali metal (such as potassium); and a crystalline aluminosilicate (such as ZSM-5) combined with a Group 10 metal (such as Pt), a Group 1 alkali metal (such as sodium), and a Group 11 metal (such as silver or copper).

Another useful catalyst composition is a Group 10 metal (such as Ni, Pd, and Pt, preferably Pt) supported on silica (e.g., silicon dioxide) modified by a Group 1 alkali metal silicate (such as Li, Na, K, Rb, and/or Cs silicates) and/or a Group 2 alkaline earth metal silicate (such as Mg, Ca, Sr, and/or Ba silicates), preferably potassium silicate, sodium silicate, calcium silicate, and/or magnesium silicate, preferably potassium silicate and/or sodium silicate. The Group 10 metal content of the catalyst composition is at least 0.005 wt %, based on the weight of the catalyst composition, preferably, in the range from about 0.005 wt % to about 10 wt %, or from about 0.005 wt % up to about 1.5 wt %, based on the weight of the catalyst composition. The silica ($SiO_2$) may be any silica typically used as catalyst support such as those marketed as DAVISIL™ 646 (Sigma Aldrich), DAVISON™ 952, DAVISON™ 948 or DAVISON™ 955 (Davison Chemical Division of W.R. Grace and Company).

The formulated catalyst composition may be made into a particle, such as, for example, a spray dried particle, an oil drop particle, a mulled particle, or a spherical particle. The formulated catalyst composition may be made into a slurry. Such slurry materials typically contain the microporous crystalline metallosilicate, such as zeolite, and a filler such as a silicate. For moving bed reactors, spherical particle shapes are particularly useful. Nonlimiting examples of formulated catalysts are described in U.S. Application No. 62/500,814, filed May 3, 2017.

For example, the catalyst material comprises platinum on ZSM-5, platinum on zeolite L, and/or platinum on silica.

In addition to the catalyst material, inert material may optionally also be present in the at least one reaction zone. As referred to herein, the inert material is understood to include materials which promote a negligible amount (e.g., less than about 3% (or 2%, or 1%, etc.)) of conversion of the feedstock, intermediate products, or final products under the reaction conditions described herein.

The catalyst material and the inert material may be combined as portions of the same particles and/or may be separate particles. The catalyst material and the inert material can be separate particles. Additionally, the catalyst material and/or inert material may be essentially spherical (i.e., less than about 20% (or 30%, or 40%, or 50%) aberration in diameter). Examples of suitable inert materials include, but are not limited to, metal carbides (e.g., silicon carbide, tungsten carbide, etc.), metal oxides (e.g., silica, zirconia, titania, alumina, etc.), clays, metal phosphates (e.g., aluminum phosphates, nickel phosphates, zirconium phosphates, etc.), and any combination thereof. In particular, the inert material may comprise silicon carbide, silica, and any combination thereof.

In addition to the catalyst material and optional inert material, transport particulate material may optionally also be present in the at least one reaction zone. As referred to herein, the transport particulate material includes materials that have selective hydrogen combustion, hydrogen storage, and/or oxidant storage functionality. The transport particulate material may be used to drive the thermodynamics of the dehydrogenation reaction by adding oxygen and/or removing hydrogen in the at least one reaction zone. The transport particulate material can comprise a metal oxide, for example a transition metal oxide, having a reversible sorptive affinity for oxidant at elevated temperature. In this context, the term "elevated temperature" means a temperature in the range of from 400° C. to 1000° C., and the term "high sorptive capacity" means an oxygen storage capacity of at least 40 millimoles of oxygen per mole of the transport particulate material that contacts the oxygen at a temperature of 800° C. Such materials include those that sorptively remove and release oxidant and those that undergo a chemical and/or physical change in the course of reversible oxidant storage. The transport particulate material can be one that stores oxidant in molecular form, e.g., as molecular oxygen, but this is not required. In any embodiment, the transport particulate material has capacity for storing and releasing oxidant in atomic or ionic form, e.g., as oxygen atoms and/or oxygen ions. In any embodiment, the transport particulate material can enable the bulk separation and purification of oxygen based on ionic transport, in which the transport particulate material is maintained at high temperature to temporarily store oxygen. Oxygen that contacts the surface of the transport particulate material can be decomposed on the surface of the material and incorporated into the crystalline lattice of the material. Storage of the oxygen can be particularly facilitated over the temperature range from 400° C. to 1000° C.

In any embodiment, when oxidant contacts the transport particulate material, oxidant (typically molecular oxygen, but not limited thereto) is adsorbed and dissociated, with charge transfer acting to cause penetrative flux of oxidant into the transport particulate material. A chemical potential driving force can be employed to effect ionic transport of oxidant into the transport particulate material.

In any embodiment, the catalyst material, the inert material, and/or the transport particulate material may individually have an average diameter of greater than or equal to about 10 μm, or 25 μm, or 50 μm, or 100 μm, or 200 μm, or 300 μm, or 400 μm, or 500 μm, or 600 μm, or 700 μm, or 800 μm, or 900 μm, or 1000 μm (e.g., about 10 μm (or 25 μm, or 50 μm, or 100 μm, or 200 μm, or 250 μm) to about 1000 μm (or about 900 μm, or about 750 μm, or about 600 μm, or about 500 μm, or about 400 μm, or about 300 μm, or about 250 μm).

For example, in a moving bed reactor, the catalyst material, the inert material, and/or the transport particulate material may individually have an average diameter of about 20 μm (or 40 μm, or 50 μm) to about 300 μm (or 100 μm, or 90 μm, or 80 μm).

The particulate material in the at least one reaction zone can be bimodal, that is the catalyst material, the inert material, and/or the transport particulate material have a different average particle diameter and/or different density such that the at least one reaction can operate in two fluidization regimes with respect to the individual group of catalyst and inert particles. In any embodiment, the catalyst material may have an average particle diameter and/or density greater than an average particle diameter and/or density of the inert material. Alternatively, the inert material may have an average particle diameter and/or density greater than an average particle diameter and/or density of the catalyst material.

Additionally, or alternatively, the difference in average particle diameter and/or density between the catalyst material and the inert material may be understood in terms of comparing a fluidization index of the catalyst material particles and a fluidization index of the inert material particles. A particle's fluidization index can be calculated according to equation (1) below:

$$\text{Fluidization Index} = \rho_p * d_p^2 \quad (1),$$

where $\rho_p$ is particle density and $d_p$ is particle diameter.

In any embodiment, the particulate material (e.g., catalyst material and inert material) in the at least one reaction zone may have the following relationship as shown in equation (2):

$$\frac{(\text{Fluidization Index})_{particle\ 1}}{(\text{Fluidization Index})_{particle\ 2}} < n, \quad (2)$$

wherein "particle 1" and "particle 2" may be the catalyst material particle or the inert material particle, provided that particle 1 and particle 2 are different and the (Fluidization Index)$_{particle\ 1}$ is <(Fluidization Index)$_{particle\ 2}$. Further, "n" may be less than about 1 (or 0.8, or 0.5). For example, particle 1 may be the catalyst material particle.

For example, the (Fluidization Index)$_{catalyst\ particle}$ can be <the (Fluidization Index)$_{inert\ particle}$. In such instances, the following relationship can occur:

$$\frac{(\text{Fluidization Index})_{catalyst\ particle}}{(\text{Fluidization Index})_{inert\ particle}} < n,$$

wherein "n" is defined as in equation (2).

In another example, the (Fluidization Index)$_{inert\ particle}$ can be <the (Fluidization Index)$_{catalyst\ particle}$. In such instances, the following relationship can occur:

$$\frac{(\text{Fluidization Index})_{inert\ particle}}{(\text{Fluidization Index})_{catalyst\ particle}} < n,$$

wherein "n" is defined as in equation (2) above.

D. Effluent

An effluent (e.g., first effluent, second effluent) exiting the at least one reaction zone may comprise a variety of hydrocarbon compositions produced in the at least one reaction zone. The hydrocarbon compositions typically have mixtures of hydrocarbon compounds, such as alkenes, alkynes, cyclic hydrocarbons, and aromatics, having from 1 (or 2 or 3 or 4 or 5 or 6) to 30 (or 24, or 10, or 6) carbon atoms. For example, when converting an acyclic $C_5$ feedstock to a product comprising cyclic $C_5$ compounds, the first effluent comprises cyclopentadiene.

The hydrocarbons produced in the at least one reaction zone may be present in a hydrocarbon portion of an effluent (e.g., first effluent, second effluent) in an amount of greater than or equal to about 20 wt %, or 30 wt %, or 40 wt %, or 50 wt %, or 60 wt %, or 70 wt %, or 80 wt %, or 90 wt % (e.g., in the range from about 20 wt % (or 25 wt %, or 30 wt %, or 35 wt %, or 40 wt %, or 45 wt %, or 50 wt %, or 55 wt %, or 60 wt %) to about 90 wt % (or 85 wt % or 80 wt % or 75 wt %, or 70 wt % or 65 wt % or 60 wt %)).

An effluent may comprise a desired hydrocarbon product and one or more other hydrocarbon products, which may be alkenes, alkynes, cyclic hydrocarbons, and aromatics. For example, when converting an acyclic $C_5$ feedstock to a product comprising cyclic $C_5$ compounds, an effluent may comprise cyclopentane and cyclopentene in addition to cyclopentadiene. The effluent may include the other hydrocarbon products at about 1.0 wt %, or 5 wt %, or 10 wt %, or 20 wt %, or 30 wt %, or 40 wt %, or 50 wt %, or 60 wt %, or 65 wt %, (e.g., in the range from about 1.0 wt % (or 5 wt %, or 10 wt %, or 15 wt %, or 20 wt %, or 25 wt %, or 30 wt %, or 35 wt %,) to about 65 wt % (or 60 wt %, or 55 wt %, or 50 wt %, or 45 wt %, or 40 wt %, or 35 wt %, or 30 wt %, or 25 wt %)).

For information on possible dispositions of the effluents, please see applications: U.S. 2017/0121243 and 2017/0121248 and U.S. Pat. Nos. 9,896,395 and 9,896,396.

E. Stripping/Separation of the Effluent

In any embodiment, catalyst material and/or inert material may become entrained with hydrocarbons (e.g., cyclopentadiene) in the effluent (e.g., first effluent, second effluent) as the effluent travels through and/or exits the at least one reaction zone. Thus, the process may further comprise separating catalyst material and/or inert material, which may be entrained with hydrocarbons (e.g., cyclopentadiene) in the effluent (e.g., first effluent, second effluent). This separating may comprise removal of the catalyst material and/or inert material from the hydrocarbons (e.g., cyclopentadiene) by any suitable means, such as, but not limited to, cyclones, filter, electrostatic precipitators, heavy liquid contacting, and/or other gas solid separation equipment, which may be inside and/or outside the at least one reaction zone. The effluent substantially free of particulate material may then travel to a product recovery system. As used herein, the term "substantially free" relative to particulate material in the effluent from a separation subsystem refers to the effluent from the separation subsystem having 10% or less particulate material as compared to the concentration of the particulate material in the effluent from the at least one reaction zone. Additionally, the separated catalyst material and/or inert material may then be fed back into the at least one reaction zone at any desirable location. A separated catalyst material stream can be introduced into the at least one reaction zone at a position above where feedstock and auxiliary gas are provided to the at least one reaction.

Additionally, or alternatively, auxiliary gas may also be separated from the effluent (e.g., first effluent, second effluent) via any suitable means or any combination thereof such as distillation, adsorption (pressure-swing or temperature-swing), membrane separation, liquid/solvent absorption, condensation, etc. and the separated auxiliary gas may be recycled back to the at least one reaction zone. The separated auxiliary gas can be heated as described above before being reintroduced into the at least one reaction zone.

Additionally, or alternatively, the separated catalyst material and/or inert material with reduced level of hydrocarbons may then travel to a rejuvenation zone, and/or regeneration zone, and the hydrocarbons stripped from the particulate material may be directed to the product recovery system or to the reactor system.

F. Rejuvenation

As the reaction occurs in the at least one reaction zone, coke material may form on the particulate material, particularly on the catalyst material, which may reduce the activity of the catalyst material. Additionally, or alternatively, the particulate material may cool as the reaction occurs. The catalyst material exiting the at least one reaction zone is referred to as "spent catalyst material." Thus, the effluent and the separate catalyst material can comprise spent catalyst material. This spent catalyst material may not necessarily be a homogenous mix of particles as individual particles may have had a distribution of total aging in the system, time since last regeneration and/or rejuvenation, and/or ratio of times spent in reaction zones relative to in the regeneration and/or rejuvenation zones.

Thus, at least a portion of the particulate material (e.g., spent catalyst material) may be transferred from the at least one reaction zone to a rejuvenation zone to produce rejuvenated catalyst material. The transferring of the particulate material (e.g., spent catalyst material) from the at least one reaction zone to a reheating zone may occur after the catalyst material has been stripped and/or separated from the hydrocarbons after exiting the at least one reaction zone. Additionally, or alternatively, catalyst (e.g., spent catalyst material) material may be transferred directly from the at least one reaction zone to a reheating zone. The reheating zone may include one or more heating devices, such as but not limited to, direct contacting, a heating coil, and/or a fired tube.

In any embodiment, in the rejuvenation zone, the particulate material (e.g., spent catalyst material) may be contacted with a gaseous stream comprising hydrogen and substantially free of reactive oxygen-containing compounds to remove at least a portion of incrementally deposited coke material on the catalyst material thereby forming a rejuvenated catalyst material and a volatile hydrocarbon, such as, but not limited to, methane. As used herein, the term "incrementally deposited" coke material refers to an amount of coke material that is deposited on the catalyst material during each pass of the catalyst material through the at least one reaction zone as opposed to a cumulative amount of coke material deposited on the catalyst material during multiple passes through the at least one reaction zone. "Substantially free" used in this context means the rejuvenation gas comprises less than about 1.0 wt %, (or 0.1 wt %, or 0.01 wt %, or 0.001 wt %, or 0.0001 wt %, or 0.00001 wt %) oxygen-containing compounds, based upon the weight of the gaseous stream. The gaseous stream may comprise greater than 50 wt % (or 60 wt %, or 70 wt %, or 90 wt %) $H_2$. The gaseous stream may further comprise an inert substance (e.g., $N_2$), and/or methane. Contacting the spent catalyst material with the gaseous stream may occur at a temperature of about 500° C. (or 575° C.) to about 900° C. (or 750° C.) and/or at a pressure between about 5 psia (or 25 psia) to about 250 psia (or 200 psia). Contacting the spent catalyst material with the gaseous stream may occur at a temperature less than the temperature of the at least one reaction zone (e.g., about 50° C. or more lower than the at least one reaction zone).

In the rejuvenation zone, the particulate material (e.g., spent catalyst material) may be rejuvenated via a mild oxidation procedure comprising contacting the particulate material with an oxygen-containing gaseous stream under conditions effective to remove at least a portion of incrementally deposited coke material on the catalyst material thereby forming a rejuvenated catalyst material. These conditions can include a temperature range of about 250° C. to about 500° C. and a total pressure of about 0.1 bar to about 100 bar. Further, the oxygen-containing gaseous stream is typically supplied to the rejuvenation zone at a total WHSV in the range of about 1 to 10,000. Following the mild oxidation, purge gas is generally reintroduced to purge oxidants from the catalyst composition using a purge gas, for example, $N_2$. This purging step may be omitted if $CO_2$ is the oxidant as it will not produce a flammable mixture. Optionally, rejuvenation via mild oxidation further comprises one or more hydrogen treatment steps.

In any embodiment, the rejuvenated catalyst material may then be returned to the at least one reaction zone.

In any embodiment, rejuvenation is generally effective at removing greater than about 10 wt % of incrementally deposited coke material (e.g., about 10 wt % (or 60 wt %, or 90 wt %) to about 100 wt % (or 95 wt %)).

Rejuvenation advantageously may have a time duration ranging from about 10 seconds (or 1 minute, or 10 minutes, or 30 minutes, or 60 minutes, or 90 minutes, or 3 hours, or 6 hours, or 12 hours, or 24 hours) to about 20 days (or 5 days, or 2 days, or 24 hours, or 12 hours, or 6 hours, or 3 hours, or 90 mins), after beginning the specified conversion process.

Rejuvenation effluent exiting the rejuvenation zone and comprising, unreacted hydrogen, coke particulate, and optionally light hydrocarbon, may be further processed. For example, where rejuvenation is achieved via contact with a hydrogen-rich gaseous stream, the rejuvenation effluent may be sent to a compression device and then sent to a separation apparatus wherein a light hydrocarbon enriched gas and light hydrocarbon depleted gas is produced. The light hydrocarbon gas may be carried away, e.g., for use as fuel gas. The light hydrocarbon depleted stream may be combined with make-up hydrogen and make up at least a portion of the gaseous stream provided to the rejuvenation zone. The separation apparatus may be a membrane system, adsorption system (e.g., pressure swing or temperature swing), or other known system for separation of hydrogen from light hydrocarbons. A particulate separation device, e.g., a cyclonic separation drum, may be provided wherein coke particulate is separated from the rejuvenation effluent.

Additional rejuvenation description is in U.S. Application No. 62/500,805, filed May 3, 2017.

G. Regeneration

The process may further comprise a regeneration step to recapture catalyst activity lost due to the accumulation of coke material and/or agglomeration of metal on the catalyst material during the reaction. This regeneration step may be carried out when there has not been sufficient removal of the coke material from the particulate material (e.g., spent catalyst material) in the rejuvenation zone.

In the regeneration step, at least a portion of the spent catalyst material from the at least one reaction zone, from the separated catalyst material following stripping from the effluent, and/or from the rejuvenation zone may be transferred to a regeneration zone and regenerated by methods known in the art. For example, an oxidative regeneration may be used to remove at least a portion of coke material from the spent catalyst material. In any embodiment, a regeneration gas comprising an oxidizing material such as oxygen, for example, air, may contact the spent catalyst material. The regeneration gas may oxidatively remove greater than or equal to 10 wt % (e.g., about 10 wt % (or 60 wt %, or 90 wt %) to about 100 wt % (or 95 wt %)) of the total amount of coke material deposited on the catalyst composition at the start of regeneration. Typically, an oxychlorination step is performed following coke removal comprising contacting the catalyst composition with a gaseous stream comprising a chlorine source and an oxygen source under conditions effective for dispersing at least a portion of metal (e.g., Group 10 metal) particles on the surface of the catalyst and to produce a metal chlorohydrate (e.g., a Group 10 metal chlorohydrate). Additionally, a chlorine stripping step is typically performed following oxychlorination comprising contacting the catalyst composition with a gaseous stream comprising an oxygen source, and optionally a chlorine source, under conditions effective for increasing the O/Cl ratio of the metal chlorohydrate. Generally, a reduction step, and optionally a sulfidation step may also be performed in the regeneration step. Typically, regeneration is effective at removing between about 10 wt % (e.g., about 25 wt %, or 60 wt %, or 90 wt %) to about 100 wt % (or 95 wt %) of coke material is removed. Optionally, before or after contacting the spent catalyst material with the regeneration gas, the catalyst material may also be contacted with a purge gas (e.g., $N_2$). Regeneration, including purging before and after coke oxidation, requires less than 10 days (or 3 days) to complete.

Catalyst may be continuously withdrawn from and returned to the reaction zone and/or the rejuvenation zone or may be periodically withdrawn from and returned to the reaction zone and/or regeneration zone. For a periodic method, typically, the regeneration times between when withdrawals are made for coke burn, oxychlorination, chlorine stripping, purge, reduction, and optional sulfidation occurs are between about 24 hours (or 1.5 days, or 2 days) to about 10 days (or 5 days). Alternatively for continuous mode, the removal/addition of particulate material rate may vary between about 0.0 wt % (or 0.01 wt %, or 0.25 wt %) to about 100 wt % (or 30 wt %) per day of the particulate material inventory, where there is balanced addition/removal of particulate material. Regeneration of the catalyst material may occur as a continuous process or may be done batch wise in both cases intermediate vessels for inventory accumulation and/or inventory discharge may be required.

The removal and addition of the particulate material (e.g., spent catalyst material, fresh catalyst material, fresh inert material, rejuvenated catalyst material, regenerated catalyst material) may occur at the same or different location in the reactor system. The particulate material (e.g., fresh catalyst material, fresh inert material, rejuvenated catalyst material, regenerated catalyst material) may be added after or before the rejuvenation zone, while the removal of the particulate material (e.g., spent catalyst material) may be done before or after the particulate material (e.g., spent catalyst material) is passed through the rejuvenation zone. At least a portion of the regenerated catalyst material may be recycled to the at least one reaction zone or at least one rejuvenation zone. For example, the regenerated catalyst material and/or fresh particulate material are provided to the rejuvenation zone to minimize any loss in heat input and to remove any remaining species that may be carried by the regenerated catalyst material from the regeneration zone. Additionally, or alternatively, separators inside or outside of the regeneration zone may be used to separate the inert material from the catalyst material prior to regeneration so that just the catalyst material is regenerated. This separation may be carried out on the basis of size, magnetic, and/or density property differences between the inert material and the regenerated catalyst material using any suitable means.

For the above-described processes, standpipes, well known by those skilled in the art with the particle size and operating conditions described above, may be used to provide the means of transporting the particulate material between the at least one reaction zone, rejuvenation zone, and/or regeneration zone. Slide valves and lifting gas, known by those skilled in the art, may also be used to help circulate the particulate material and/or build the necessary pressure profile inside the regeneration zone. The lifting gas may be the same as the fluidizing gas used in the rejuvenation zone, e.g., a hydrogen stream that may contribute in minimizing the hydrogen usage in the reaction system, while also reducing the coke material formation.

Additional rejuvenation description is in US Patent Application No. 62/500,795, filed May 3, 2017.

III. Reaction Systems for Conversion of Hydrocarbons

FIG. 1A shows an example of an endothermic dehydrogenation reactor system 100 that includes a catalyst regeneration and/or regeneration subsystem 110, a heat exchanger 118, and moving bed reactor 111 having at least one reaction zone 112 and a separation subsystem 113 downstream of the at least one reaction zone 112.

The moving bed reactor 111 is adapted for (i) receiving a feedstock stream 114 (and optionally an auxiliary gas stream, not illustrated) to the at least one reaction zone 112 in the moving bed reactor 111 and (ii) receiving a rejuvenated and/or regenerated catalyst stream 115 to the at least one reaction zone 112 and from the catalyst rejuvenation and/or regeneration subsystem 110. The moving bed reactor 111 may optionally include one or more internal structures (e.g., baffles, sheds, trays, tubes, tube bundles, tube coils, rods, and/or distributors) to influence a velocity vector of the particulate material and/or hydrocarbon fluid flow within the moving bed reactor 111.

The separation subsystem 113 may be useful in performing the above-described process in Section E. Stripping/Separation of the Effluent. The illustrated separation subsystem 113 is adapted for (i) receiving a particulate-laden effluent stream 121 (e.g., comprising catalyst particles and, optionally, inert particles and/or transport material particles) from the at least one reaction zone 112, (ii) supplying a substantially particulate-free effluent stream 117, and (iii) supplying a separated particulate stream 122 to the at least one reaction zone 112 (or alternatively to the catalyst rejuvenation and/or regeneration subsystem 110, not illustrated). Examples of separation subsystems comprise components/portions that include, but are not limited to, one or more separators, one or more cyclone particle separators, one or more disengaging components or vessels, one or more plates, one or more caps, one or more elbows, one or more filters, one or more electrostatic precipitators, and/or one or more other gas solid separation equipment components. While the illustrated system includes the separation subsystem 113 as in the reactor 111, the two may be separated with appropriate fluid connection to (i) supply the particulate-laden effluent stream 121 from the at least one reaction zone 112 to the separation subsystem 113 and (ii) supply the reactor 111 and/or catalyst rejuvenation and/or regeneration subsystem 110 with the separated particulate stream 122 from the separation subsystem 113.

The catalyst rejuvenation and/or regeneration subsystem 110 may be useful in performing the above-described processes in section F. Rejuvenation and G. Regeneration. The illustrated catalyst regeneration subsystem 110 is adapted for (i) receiving a spent catalyst stream 116 to the moving bed reactor 111. Examples of catalyst rejuvenation and/or regeneration subsystem comprise components/portions that include, but are not limited to, one or more spent catalyst accumulation vessel, one or more catalyst rejuvenation and/or regeneration vessels, one or more stripping portions, and any combination thereof. While the illustration shows the rejuvenation and/or regenerated catalyst stream 115 and the spent catalyst stream 116 near the bottom of the at least one reaction zone 112 and on the same side of the reactor 111, each may individually fluidly connect to the at least one reaction zone 112 at any location.

The heat exchanger 118 is illustrated as in the at least one reaction zone 112. The heat exchanger 118 is adapted to receive a heat exchanger feed stream 119 (comprising heating medium) and supply a heat exchanger effluent stream 120. The heat exchanger 118 is further adapted so that the heating medium passing through the heat exchanger 118 does not contact that the catalyst, the feedstock, and the product in the at least one reaction zone 112. The heat exchanger 118 and heating medium therein supply heat to the at least one reaction zone. The heat exchanger 118 may be configured in a number of ways including, but not limited to, the examples in FIGS. 1B-1D. While the illustration shows the heat exchanger feed stream 119 and the heat exchanger effluent stream 120 near the top of the at least one reaction zone 112 and on opposing side of the reactor 111, each may individually fluidly connect to the heat exchanger 118 at any location.

Examples of heating medium may include, but are not limited to, steam, combustion product (e.g., flue gas), hot gas, molten salt, molten metal, etc.

Figure 1C:
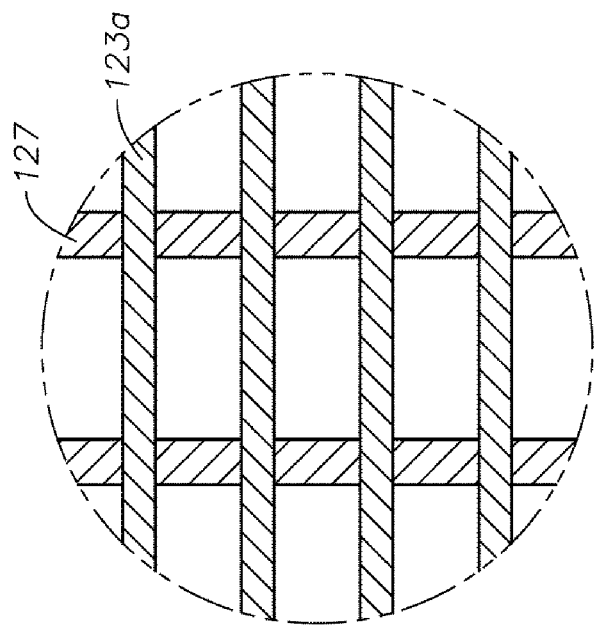
FIG. 1C shows a top view of the example configuration of the heat exchanger of FIG. 1B.
Figure 1B:
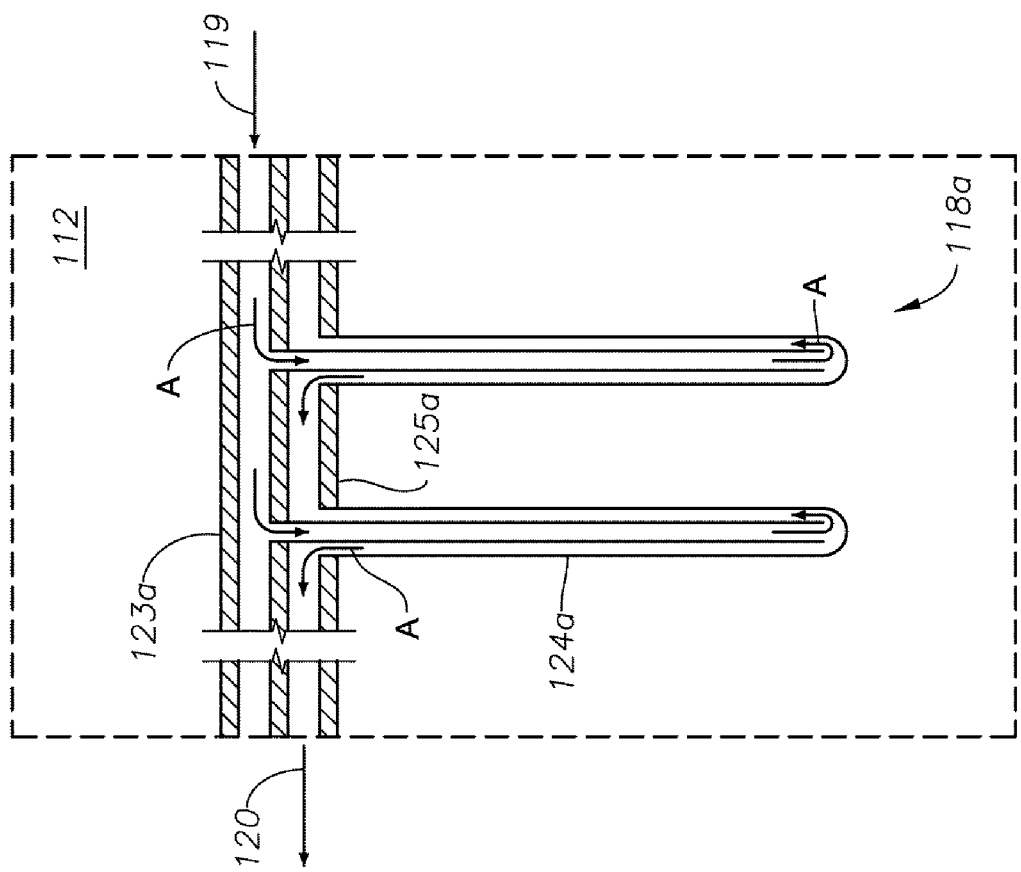
FIG. 1B shows an example configuration of a heat exchanger in a vertical, top-feed configuration.

FIG. 1B, with continued reference to FIG. 1A, shows an example configuration of a heat exchanger 118a in a vertical, top-feed configuration. In this illustration as indicated by the arrows A, the heat exchanger feed stream 119 enters a first header 123a, passes through vertical bayonet tubes 124a, and enters a second header 125a that supplies to the heat exchanger effluent stream 120. The first and second headers 123a and 125a in vertical, top-feed configuration are positioned at a height in the reactor 111 sufficient to allow the vertical bayonet tubes 124a to extend downward from the first and second headers 123a and 125a. The first and second headers 123a and 125a are configured to allow the moving bed reactor 111 to operate in a desired particulate movement regime.

While the illustration shows the first and second headers 123a and 125a as horizontal and the vertical bayonet tubes 124a as vertical, each or portions of each may individually be angled (e.g., by about 30° or less) off-horizontal or off-vertical, respectively. Further, the first and second headers 123a and 125a and the vertical bayonet tubes 124a are generally illustrated as straight. However, curved structures may also be used. While the illustration shows that the heating media first flows through the inner most tube and then through the annular space it may also flow in the opposite configuration; i.e., first though the annular space and then through the inner tube.

FIG. 1C, with continued reference to FIGS. 1A and 1B, is a top view of a portion of the heat exchanger 118a. The first headers 123a are illustrated as being held in place with braces 127, which may mitigate vibration of the vertical bayonet tubes 124a. Additional braces and fasteners (not illustrated) may be included to secure the heat exchanger 118a and mitigate vibration thereof.

Figure 1E:
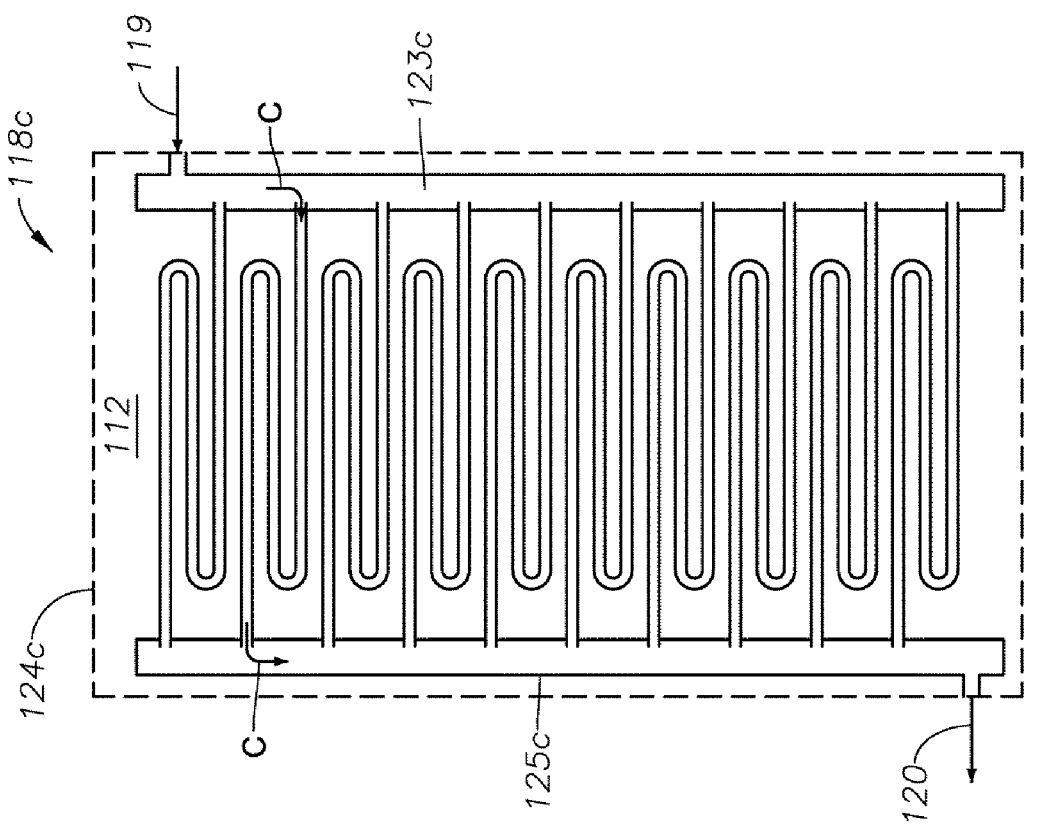
FIG. 1E shows yet another example configuration of a heat exchanger in a horizontal configuration.
Figure 1D:
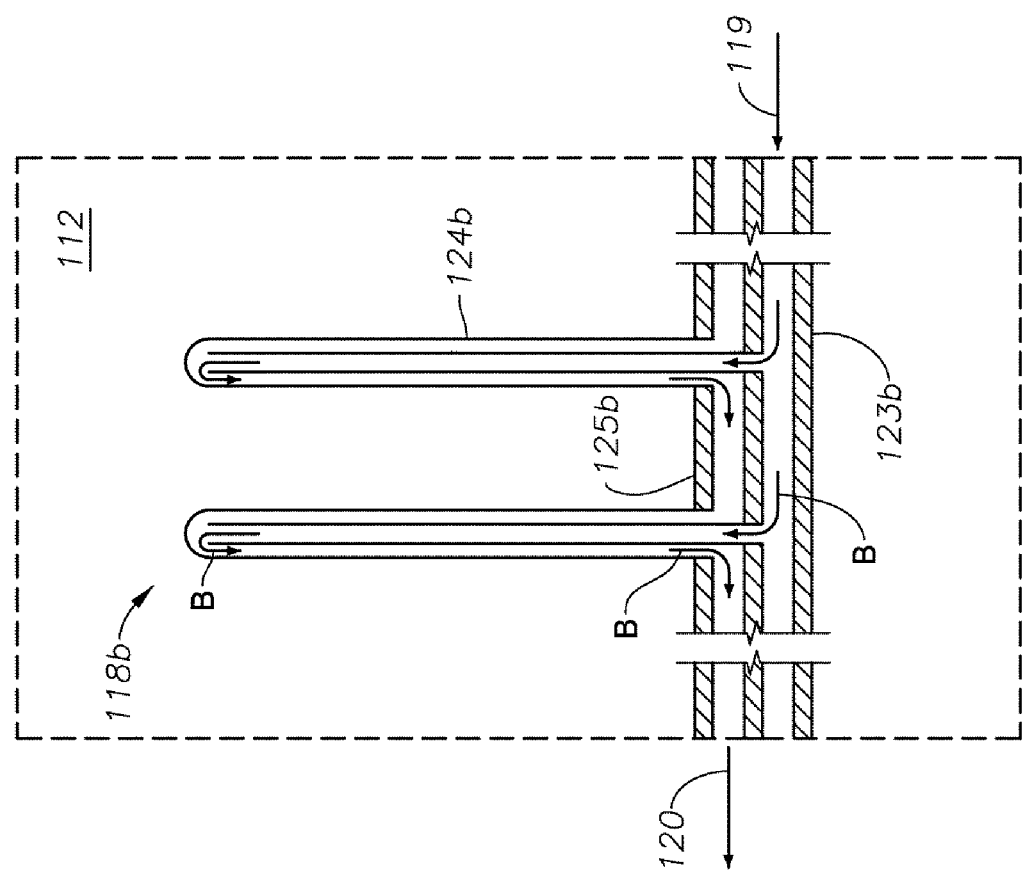
FIG. 1D shows another example configuration of a heat exchanger in a vertical, bottom-feed configuration.

FIG. 1D, with continued reference to FIG. 1A, shows another example configuration of a heat exchanger 118b in a vertical, bottom-feed configuration. In this illustration as indicated by the arrows B, the heat exchanger feed stream 119 enters a first header 123b, passes through vertical bayonet tubes 124b, and enters a second header 125b that supplies to the heat exchanger effluent stream 120. The first and second headers 123b and 125b in vertical, bottom-feed configuration are positioned at a height in the reactor 111 sufficient to allow the vertical bayonet tubes 124b to extend upward from the first and second headers 123b and 125b. The first and second headers 123b and 125b are configured to allow the moving bed reactor 111 to operate in a desired particulate movement regime.

While the illustration shows the first and second headers 123b and 125b as horizontal and the vertical bayonet tubes 124b as vertical, each or portions of each may individually be angled (e.g., by about 30° or less) off-horizontal or off-vertical, respectively. Further, the first and second headers 123b and 125b and the vertical bayonet tubes 124a are generally illustrated as straight. However, curved structures may also be used.

Additionally, braces and fasteners (not illustrated) may be included to secure the heat exchanger 118b and mitigate vibration thereof.

FIG. 1E, with continued reference to FIG. 1A, shows yet another example configuration of a heat exchanger 118c in a horizontal configuration. In this illustration as indicated by the arrows C, the heat exchanger feed stream 119 enters a first header 123c, passes through horizontal tubes 124c, and enters a second header 125c that supplies to the heat exchanger effluent stream 120. The horizontal tubes 124c in horizontal configuration are configured to have sufficient room therebetween to allow the moving bed reactor 111 to operate in the desired particulate movement regime.

While the illustration shows the first and second headers 123c and 125c as vertical and the horizontal tubes 124c as horizontal, each or portions of each may individually be angled (e.g., by about 30° or less) off-vertical or off-horizontal, respectively. Further, the first and second headers 123c and 125c are generally illustrated as straight, and the horizontal tubes 124c are illustrated as curved and snaking between the two headers 123c and 125c. However, other structures and configurations may also be used.

Additionally, braces and fasteners (not illustrated) may be included to secure the heat exchanger 118c and mitigate vibration thereof.

Figure 1F:
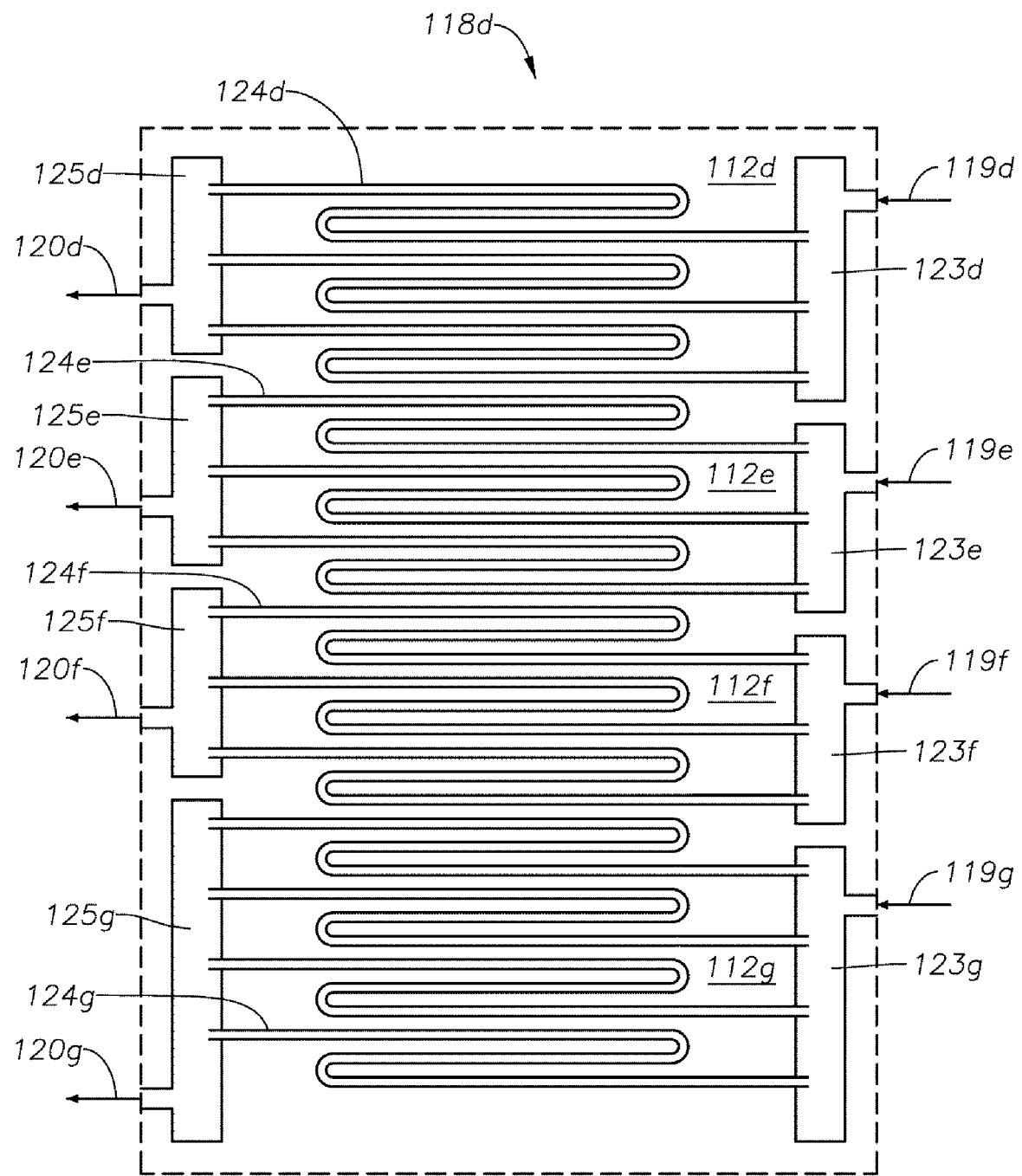
FIG. 1F shows yet another example configuration of a heat exchanger in a horizontal, staged configuration.

FIG. 1F, with continued reference to FIG. 1A, shows yet another example configuration of a heat exchanger 118d in a horizontal, staged configuration. In this example, the heat exchanger 118d includes four sets of tubes 124d-g with corresponding first headers 123d-g having heat exchanger feed streams 119d-g and second headers 125d-g having heat exchanger effluent streams 120d-g. Optionally, the heat exchanger effluent streams 120d-g may all be combined in the reactor or outside the reactor to produce a single heat exchanger effluent stream (not illustrated). Each of the heat exchanger feed streams 119d-g may be at different temperatures so as to create four reaction zones 112d-g. For example, the temperature of the heat exchanger feed streams 119d-g may increase for higher reaction zones 112d-g (i.e., $T_{112d} > T_{112e} > T_{112f} > T_{112g}$). At lower temperatures, the selectivity of the dehydrogenation reaction is higher. At higher temperature, the yield of the dehydrogenation reaction is higher. Therefore, in this example, the dehydrogenation reaction may be driven initially to high selectivity and then to high yield to react the remaining reactants.

While the illustration in FIG. 1F shows the first and second headers 123*d-g* and 125*d-g* as vertical and the horizontal tubes 124*d-g* as horizontal, each or portions of each may individually be angled (e.g., by about 30° or less) off-vertical or off-horizontal, respectively. Further, the first and second headers 123*d-g* are generally illustrated as straight and similarly positioned radially from the center of the reactor, and the horizontal tubes 124*d-g* are illustrated as curved and snaking between their respective headers 123*d-g* and 125*d-g*. However, other structures and configurations may be used.

Additionally, braces and fasteners (not illustrated) may be included to secure the heat exchanger 118*d* and mitigate vibration thereof.

Figure 1G:
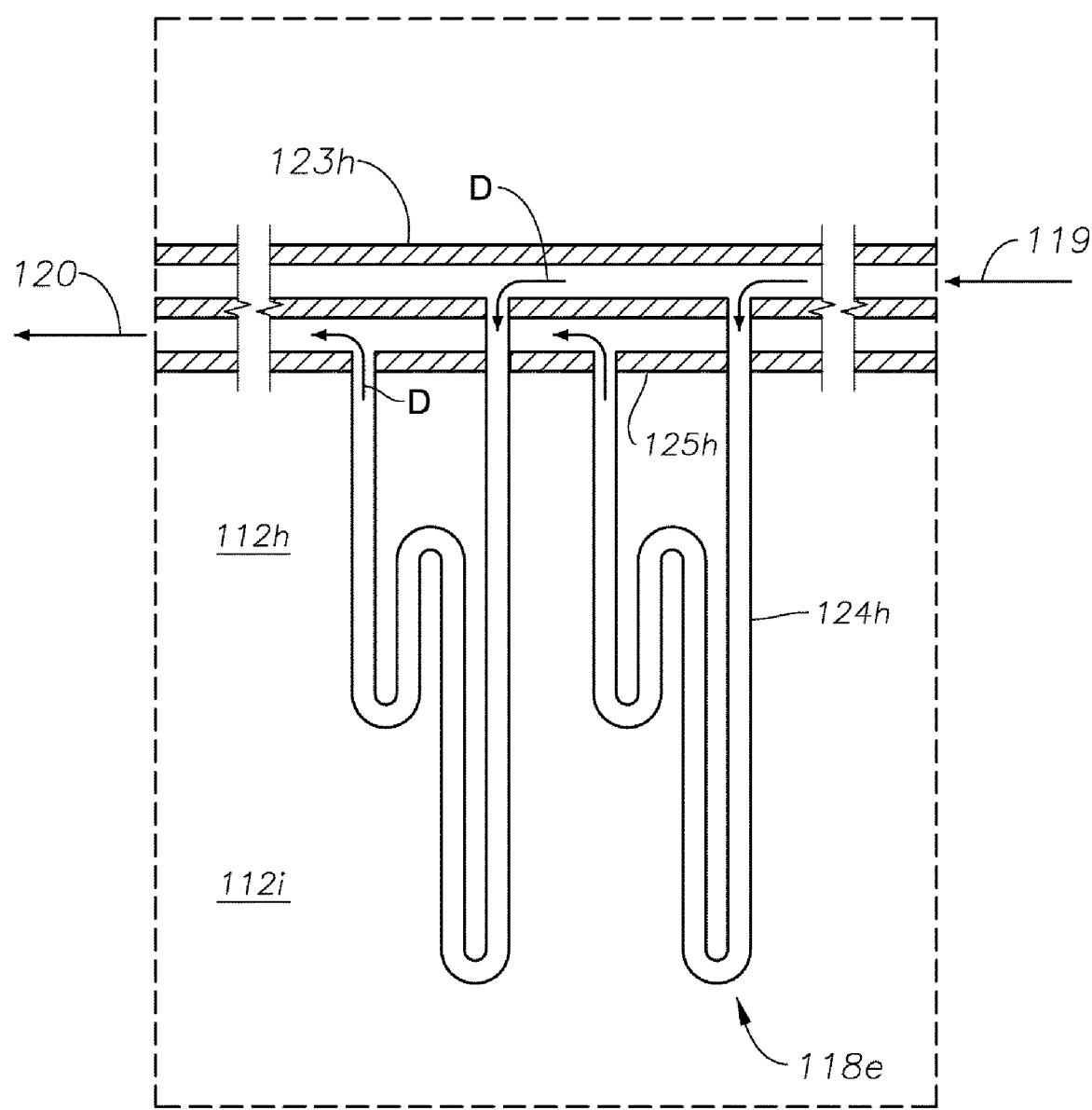
FIG. 1G shows another example configuration of a heat exchanger in a vertical, staged configuration.

FIG. 1G, with continued reference to FIG. 1A, shows yet another example configuration of a heat exchanger 118*e* in a vertical, staged configuration. In this example, the heat exchanger 118*e* includes tubes 124*h* with corresponding first header 123*h* having heat exchanger feed stream 119 and second header 125*h* having heat exchanger effluent stream 120. Heating fluid flow is illustrated with arrows D. The tubes 124*h* are illustrated as U-tubes that extend different distances into the at least one reaction zone. In the illustration, the tubes 124*h* extend to two different distances and create two reaction zones 112*h* and 112*i*. Because more of the heating fluid is in thermal contact with the gas in the top reaction zone 112*h*, the temperature in the top reaction zone 112*h* will be hotter than the bottom reaction zone 112*i*.

Figure 2:
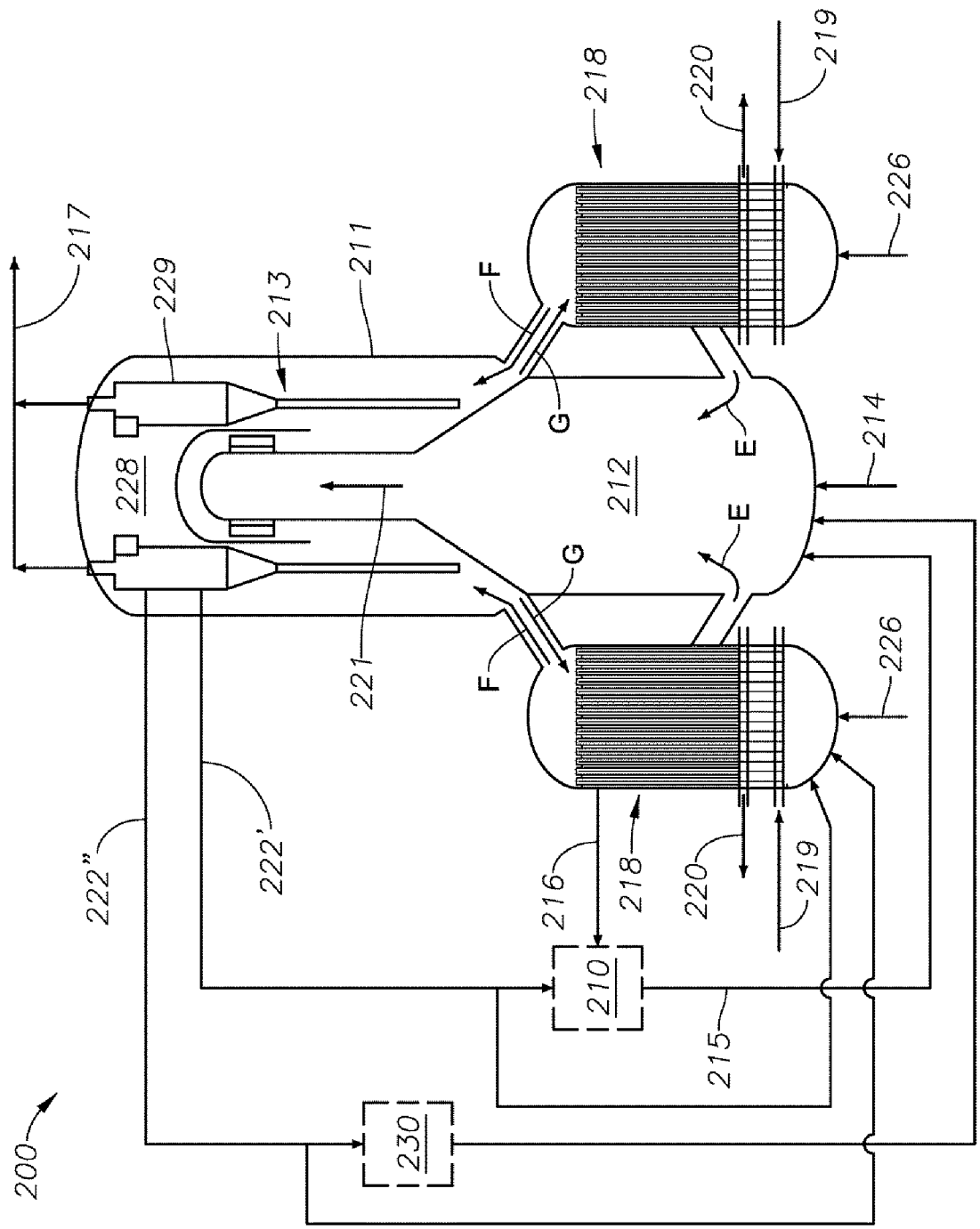
FIG. 2 shows another example of an endothermic dehydrogenation reactor system.

FIG. 2 shows another example of an endothermic dehydrogenation reactor system 200 that includes a catalyst regeneration subsystem 210, a heat exchanger 218, and moving bed reactor 211, where like numbers to FIG. 1A or other figures of the current disclosure refer to similar components.

In this example, the heat exchanger 218 (illustrated in a U-tubes in a vertical, bottom-feed configuration) is separate from or external to the reactor 211. In this configuration, the catalyst material mixes with an auxiliary gas stream 226 in the heat exchanger 218. A majority of the catalyst and a minor portion of the auxiliary gas transported to the reactor 211 per arrows E to mix with the feedstock stream 214 in the at least one reaction zone 212. The flow of the auxiliary gas stream 226 is sufficient to have majority flow also along arrows F to ensure the feedstock and/or product minimally (or do not) enter the heat exchanger 218.

FIG. 2 also illustrates an example of a separation subsystem 213. The separation subsystem 213 includes a disengaging zone 228 that receives the particulate-laden effluent stream 221 from the at least one reaction zone 212). In the disengaging zone 228, at least some of the particulates (e.g., those with higher density or size) can separate from the particulate-laden effluent stream 221, collect in the bottom of the separation subsystem 213, and re-enter the heat exchanger 218 per arrows G, which are counter to the flow of arrows F. Additional particulates are be removed from the particulate-laden effluent stream 221 using cyclones 229 to produce (1) substantially particulate-free effluent stream 217 and (2) one or more separated particulate streams (illustrated as two separated particulate stream 222' and 222"). In embodiments with more than one type of particulate (e.g., catalyst material, and inert material, and/or transport particulate material), the cyclones 229 may further separate the types of particulates based on size and/or density. As illustrated, the first separated particulate stream 222' includes primarily catalyst material, which (1) when regenerated and/or rejuvenated in the catalyst regeneration subsystem 210 is transported back to the moving bed reactor 211 or (2) when not regenerated and/or rejuvenated is transported back the heat exchanger 218. As illustrated, the second separated particulate stream 222" includes primarily another type of particulate, which (1) when restored in a restoration subsystem 230 is transported to the moving bed reactor 211 or (2) when not restored is transported back to the heat exchanger 218. For example, when the second separated particulate stream 222" includes transport particulate material, the restoration subsystem 230 may add oxygen to and/or remove hydrogen from the transport particulate material. The foregoing examples of particulate flow can be modified to include all particulates whether regenerated, rejuvenated, and/or restored flow to the heat exchanger 218 or the moving bed reactor 211.

Figure 3:
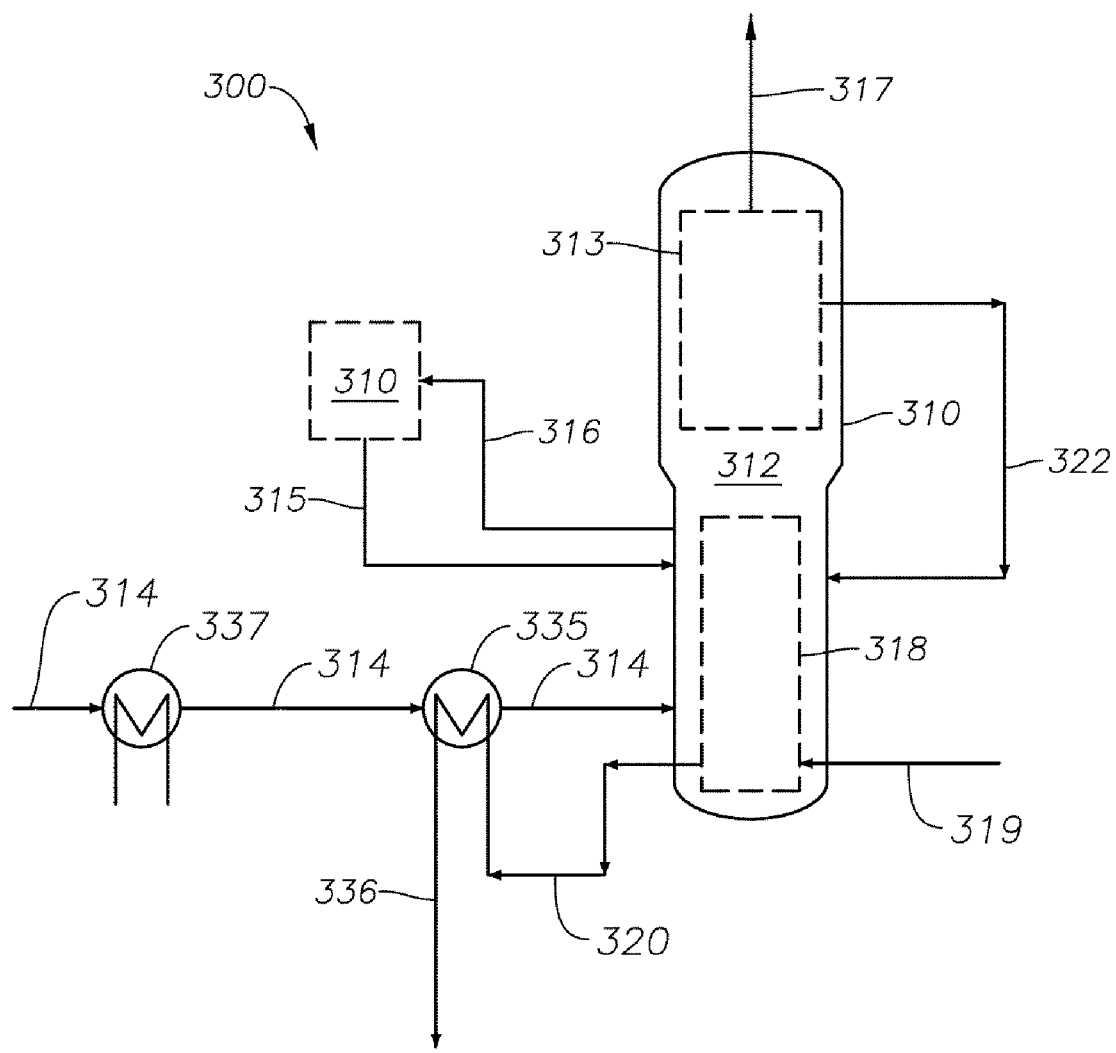
FIG. 3 shows another example of an endothermic dehydrogenation reactor system.

FIG. 3 shows another example of an endothermic dehydrogenation reactor system 300 that includes a catalyst regeneration subsystem 310, a heat exchanger 318, and moving bed reactor 311, where like numbers to FIG. 1A or other figures of the current disclosure refer to similar components. In this examples, a feedstock stream 314 is heated using a heat exchanger effluent stream 320. Optionally, when an auxiliary gas stream is included, the heat exchanger effluent stream 320 may be used additionally or alternatively to heat the auxiliary gas stream.

FIG. 3, more specifically, illustrates that the heat exchanger effluent stream 320 passes through an external heat exchanger 335 that also has passing through the feedstock stream 314 (in different portions in heat, not fluid communication). The feedstock stream 314 increases in temperature. The heat exchanger effluent stream 320 reduces in temperature and leaves the external heat exchanger 335 as an external heat exchanger effluent stream 336.

Additionally illustrated is a waste heat exchanger 337 upstream along the feedstock stream 314 of the external heat exchanger 335. The waste heat exchanger 337 increases the temperature of the feedstock stream 314, which is then further increased by the external heat exchanger 335. The waste heat exchanger 337 may use waste heat from another process in the facility to heat the feedstock stream 314.

Figure 4:
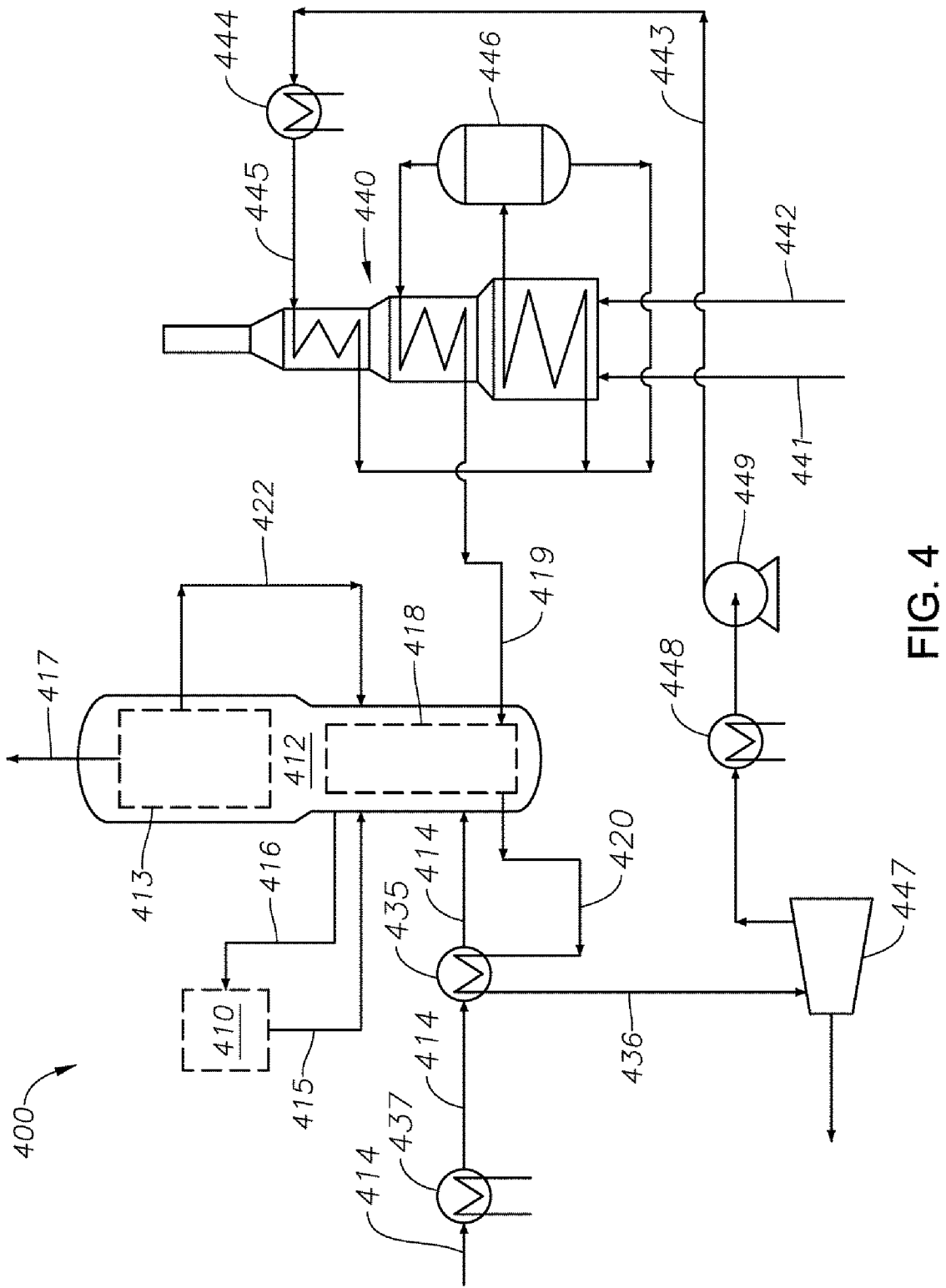
FIG. 4 shows another example of an endothermic dehydrogenation reactor system.

FIG. 4 shows another example of an endothermic dehydrogenation reactor system 400 that includes a catalyst regeneration subsystem 410, a heat exchanger 418, and moving bed reactor 411, where like numbers to FIG. 1A or other figures of the current disclosure refer to similar components. This figure further illustrates an example of a flow path of the heating medium through a furnace 440 used to heat heating medium before introduction to the heat exchanger 418.

The furnace 440 reacts natural gas and/or processed fuel gas 441 and air 442 to heat a condensate stream 443. The condensate stream is optionally preheated with waste heat in a second waste heat exchanger 444 similar to waste heat exchanger 437 to produce heated condensate stream 445. The heated condensate stream 445 is passed through the furnace 440 and a separator 446 several times to produce the heat exchanger feed stream 419.

The heat exchanger feed stream 419 follows a similar path as FIG. 3 to become an external heat exchanger effluent stream 436 that is then expanded with turbine 447 to recover shaft work and cooled with cooling heat exchanger 448 and transported with pump 449 to produce the condensate stream 443.

IV. Industrial Applicability

A first hydrocarbon reactor effluent obtained during the acyclic $C_5$ conversion process containing cyclic, branched and linear C<sub>5</sub> hydrocarbons and, optionally, containing any combination of hydrogen, C<sub>4</sub> and lighter byproducts, or C<sub>6</sub> and heavier byproducts is a valuable product in and of itself. For example, CPD and/or DCPD may be separated from the reactor effluent to obtain purified product streams which are useful in the production of a variety of high value products.

For example, a purified product stream containing greater than or equal to about 50 wt % (or 60 wt %) of DCPD is useful for producing hydrocarbon resins, unsaturated polyester resins, and epoxy materials. A purified product stream containing greater than or equal to about 80 wt % (or 90 wt %) of CPD is useful for producing Diels-Alder reaction products formed in accordance with the following reaction Scheme (I):

Scheme I

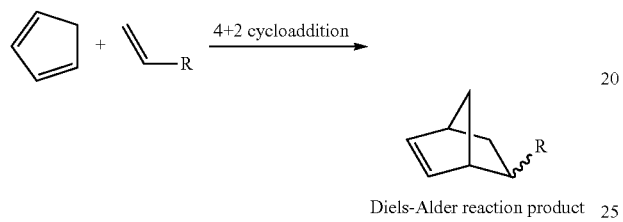

Diels-Alder reaction product where R is a heteroatom or substituted heteroatom, substituted or unsubstituted $C_1$-$C_{50}$ hydrocarbyl radical (often a hydrocarbyl radical containing double bonds), an aromatic radical, or any combination thereof. For example, substituted radicals or groups contain one or more elements from Groups 13-17 (or from Groups 15 or 16, or nitrogen, or oxygen, or sulfur). In addition to the mono-olefin Diels-Alder reaction product depicted in Scheme (I), a purified product stream containing greater than or equal to about 80 wt % (or 90 wt %) of CPD can be used to form Diels-Alder reaction products of CPD with one or more of the following: another CPD molecule, conjugated dienes, acetylenes, allenes, disubstituted olefins, trisubstituted olefins, cyclic olefins, and substituted versions of the foregoing. Preferred Diels-Alder reaction products include norbornene, ethylidene norbornene, substituted norbornenes (including oxygen-containing norbornenes), norbornadienes, and tetracyclododecene, as illustrated in the following structures:

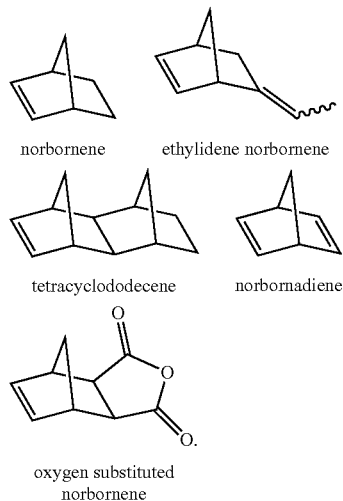

The foregoing Diels-Alder reaction products are useful for producing polymers and copolymers of cyclic olefins copolymerized with olefins such as ethylene. The resulting cyclic olefin copolymer and cyclic olefin polymer products are useful in a variety of applications, e.g., packaging film.

A purified product stream containing 99 wt % or greater of DCPD is useful for producing DCPD polymers using, for example, ring opening metathesis polymerization (ROMP) catalysts. The DCPD polymer products are useful in forming articles, particularly molded parts, e.g., wind turbine blades and automobile parts.

Additional components may also be separated from the reactor effluent and used in the formation of high value products. For example, separated cyclopentene is useful for producing polycyclopentene, also known as polypentenamer, as depicted in Scheme (II).

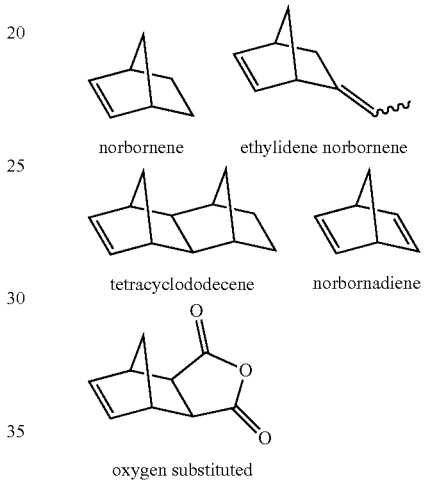

Scheme II

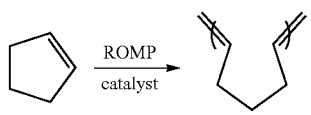

Separated cyclopentane is useful as a blowing agent and as a solvent. Linear and branched C<sub>5</sub> products are useful for conversion to higher olefins and alcohols. Cyclic and non-cyclic C<sub>5</sub> products, optionally after hydrogenation, are useful as octane enhancers and transportation fuel blend components.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Prophetic Examples

The following examples are derived from modeling techniques and although the work was actually achieved, the inventors do not present these examples in the past tense to comply with M.P.E.P. § 608.01(p) if so required.

Referring again to FIG. 4, Table 1 provides example temperature and pressure for the various streams of the endothermic dehydrogenation reactor system 400 where the 440 has a steam generating capacity of about 162 T/hr and the reactor 410 is for CPD production.

TABLE 1

| Stream | Temperature (° C.) | Pressure (bar) |
|---|---|---|
| heat exchanger feed stream 419 | 900-1050 | 10-20 |
| heat exchanger effluent stream 420 | 600-700 | 9-14 |
| external heat exchanger effluent stream 436 | 400-500 | 8-13 |
| condensate stream 443 | 25-75 | 11-16 |
| heated condensate stream 445 | 100-150 | 11-16 |
| feedstock stream 414 between waste heat exchanger 437 and external heat exchanger 435 | 200-300 | |
| feedstock stream 414 after external heat exchanger 435 | 450-550 | |
| substantially catalyst-particulate effluent stream 417 | 525-625* | |

*The substantially catalyst-particulate effluent stream 417 is at a greater temperature than the feedstock stream 414 after external heat exchanger 435.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. For example, the compositions described herein may be free of any component, or composition not expressly recited or disclosed herein. Any method may lack any step not recited or disclosed herein. Likewise, the term "comprising" is considered synonymous with the term "including." And whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A process for endothermic dehydrogenation, the process comprising:
    disposing a catalyst material in a moving bed reactor having at least one reaction zone, the moving bed reactor comprising a heat exchanger containing a heating medium, wherein the catalyst material and the heating medium do not directly contact one another, and wherein at least 50% of delta enthalpy of the at least one reaction zone is provided by transfer of heat through the heat exchanger to the catalyst material; and
    contacting a feedstock comprising hydrocarbons with the catalyst material in the at least one reaction zone of the moving bed reactor under reaction conditions to convert at least a portion of the hydrocarbons to a first effluent comprising a product comprising alkenes, alkynes, cyclic hydrocarbons, and/or aromatics.

2. The process of claim 1 further comprising:
    separating at least some of the catalyst material from the first effluent to produce (1) a separated catalyst stream and (2) a product stream; and
    returning the separated catalyst material to the moving bed reactor.

3. The process of claim 2, wherein the product stream is substantially catalyst-free.

4. The process of claim 2, wherein the product stream exits the moving bed reactor at an outlet temperature of about 350° C. to about 800° C., wherein a cumulative exposure time of a hydrocarbon fluid phase to temperatures 50° C. greater than the outlet temperature is less than 10% of total exposure time, and wherein a cumulative exposure time of the catalyst material to temperatures 50° C. greater than the outlet temperature is less than 10% of total catalyst material time in the moving bed reactor.

5. The process of claim 1, wherein the heat exchanger traverses at least a portion of the at least one reaction zone.

6. The process of claim 1, wherein the heat exchanger does not traverse the at least one reaction zone.

7. The process of claim 1, wherein the heat exchanger comprises a heat transfer conduit.

8. The process of claim 7, wherein the heat transfer conduit comprises a plurality of bayonet tubes in a vertical, bottom-feed configuration.

9. The process of claim 7, wherein the heat transfer conduit comprises a plurality of bayonet tubes in a vertical, top-feed configuration.

10. The process of claim 7, wherein the heat transfer conduit comprises a plurality of tubes in a horizontal, staged configuration.

11. The process of claim 7, wherein the heat transfer conduit is braced.

12. The process of claim 1, wherein at least one baffle is present in the at least one reaction zone.

13. The process of claim 12, wherein the at least one reaction zone includes two reaction zones at different temperatures and on opposing sides of the baffle.

14. The process of claim 1, further comprising contacting the heat exchanger with an auxiliary gas stream combined with the feedstock, wherein the auxiliary gas stream comprises steam, inert gas, hydrogen, and/or light hydrocarbons, wherein the auxiliary gas stream and the heating medium do not contact.

15. The process of claim 1, further comprising transporting the catalyst material between a first zone of the moving bed reactor and a second zone of the moving bed reactor, wherein in the first zone the catalyst material contacts the feedstock, and wherein in the second zone the catalyst material contacts the heat exchanger and an auxiliary gas stream, wherein the auxiliary gas stream comprises steam, inert gas, hydrogen, and/or light hydrocarbons, wherein the auxiliary gas stream and the heating medium do not contact.

16. The process of claim 14, further comprising preheating the auxiliary gas stream to a temperature of about 300° C. to about 900° C. before contacting the heat transfer conduit.

17. The process of claim 1, wherein the reaction conditions comprise a temperature of about 500° C. to about 700° C. and a pressure of about 3 psia to about 100 psia.

18. The process of claim 1, wherein the catalyst material comprises at least one metal or metal compound comprising at least one selected from the group consisting of V, Nb, Ta, Cr, Mo, W, Mn, Re, Fe, Ru, Os, Co, Rh, Ir, Ni, Pd, Pt, Cu, Ag, Au, Zn, Cd, Al, Ga, In, Tl, Ge, Sn, Pb, and any combination thereof.

19. The process of claim 1, further comprising transferring at least a portion of the catalyst material to a rejuvenation zone and/or a regeneration zone to produce a rejuvenated catalyst material and/or a regenerated catalyst material; and returning at least a portion of the rejuvenated catalyst material and/or the regenerated catalyst material to the at least one reaction zone.

20. The process of claim 19, wherein the rejuvenation zone and/or the regeneration zone is at a lower temperature than the at least one reaction zone.

21. The process of claim 19, further comprising providing fresh catalyst material to the at least one reaction zone, the regeneration zone, and/or the rejuvenation zone.

22. The process of claim 19, further comprising at least partially removing coke from the catalyst material in the regeneration zone, and/or the rejuvenation zone.

23. The process of claim 19, further comprising redispersing the catalyst in the regeneration zone, and/or the rejuvenation zone.

24. The process of claim 1, wherein the hydrocarbons comprise acyclic $C_5$ hydrocarbons, and the cyclic hydrocarbons comprise cyclopentadiene.

25. The process of claim 24, wherein at least about 30 wt % of the acyclic $C_5$ hydrocarbons is converted to cyclopentadiene.

* * * * *